United States Patent
Ogle et al.

(10) Patent No.: US 10,463,386 B2
(45) Date of Patent: Nov. 5, 2019

(54) THROMBECTOMY DEVICES AND TREATMENT OF ACUTE ISCHEMIC STROKE WITH THROMBUS ENGAGEMENT

(71) Applicant: MIVI Neuroscience Inc., Eden Prairie, MN (US)

(72) Inventors: Matthew F. Ogle, Edina, MN (US); Lee R. Gutterman, Amherst, NY (US); Richard C. Mattison, Zimmerman, MN (US)

(73) Assignee: MIVI Neuroscience, Inc., Eden Prairie, MN (US)

( * ) Notice: Subject to any disclaimer, the term of this patent is extended or adjusted under 35 U.S.C. 154(b) by 373 days.

(21) Appl. No.: 15/253,202

(22) Filed: Aug. 31, 2016

(65) Prior Publication Data
US 2017/0056061 A1    Mar. 2, 2017

Related U.S. Application Data

(60) Provisional application No. 62/212,773, filed on Sep. 1, 2015.

(51) Int. Cl.
*A61B 17/3207* (2006.01)
*A61B 17/221* (2006.01)
(Continued)

(52) U.S. Cl.
CPC .... *A61B 17/320725* (2013.01); *A61B 17/221* (2013.01); *A61F 2/013* (2013.01);
(Continued)

(58) Field of Classification Search
CPC ................. A61F 2/013; A61F 2002/011; A61F 2002/015; A61F 2002/016; A61F 2002/018; A61B 17/221
See application file for complete search history.

(56) References Cited

U.S. PATENT DOCUMENTS 4,610,662 A    9/1986 Weikl et al.
4,723,549 A    2/1988 Wholey et al.
(Continued)

FOREIGN PATENT DOCUMENTS

JP    2000-508954 A    7/2000
JP    2003-530903 A    10/2003
(Continued)

OTHER PUBLICATIONS

International Search Report and Written Opinion from co-pending application, PCT/US2016/49723, dated Jan. 17, 2017 (14 pages).
(Continued)

*Primary Examiner* — Robert A Lynch
(74) *Attorney, Agent, or Firm* — Christensen, Fonder, Dardi & Herbert PLLC; Peter S. Dardi

(57) ABSTRACT

Components and corresponding systems are described for providing removal of a clot or fragment thereof to address an acute ischemic stroke condition. In particular, a filter design is presented that provides metal elements below a bundle of polymer fibers to provide more mechanical strength while cushioning the vessel wall from direct contact with the metal elements. Designs of stent retrievers are presented with polymer covers or mounted on the exterior of a microcatheter. Corresponding systems are described that can use various combinations of the components, generally in combination with an aspiration catheter. Corresponding procedures are described that can effectively use the various devices and systems.

13 Claims, 18 Drawing Sheets

(51) Int. Cl.
*A61F 2/01* (2006.01)
*A61B 17/22* (2006.01)
*A61B 90/00* (2016.01)

(52) U.S. Cl.
CPC .............. *A61B 2017/2212* (2013.01); *A61B 2017/2215* (2013.01); *A61B 2017/22035* (2013.01); *A61B 2090/0811* (2016.02); *A61F 2002/016* (2013.01)

(56) References Cited

U.S. PATENT DOCUMENTS

| | | |
|---|---|---|
| 4,728,319 A | 3/1988 | Masch |
| 4,784,636 A | 11/1988 | Rydell |
| 4,790,812 A | 12/1988 | Hawkins, Jr. et al. |
| 4,794,928 A | 1/1989 | Kletschka |
| 4,873,978 A | 10/1989 | Ginsburg |
| 4,883,460 A | 11/1989 | Zanetti |
| 4,887,613 A | 12/1989 | Farr et al. |
| 4,994,067 A | 2/1991 | Summers |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,100,425 A | 3/1992 | Fischell et al. |
| 5,102,415 A | 4/1992 | Guenther et al. |
| 5,108,419 A | 4/1992 | Reger et al. |
| 5,152,277 A | 10/1992 | Honda et al. |
| 5,163,906 A | 11/1992 | Ahmadi |
| 5,200,248 A | 4/1993 | Thompson et al. |
| 5,211,651 A | 5/1993 | Reger et al. |
| 5,462,529 A | 10/1995 | Simpson et al. |
| 5,549,626 A | 8/1996 | Miller et al. |
| 5,599,307 A | 2/1997 | Bacher et al. |
| 5,720,764 A | 2/1998 | Naderlinger |
| 5,766,191 A | 6/1998 | Trerotola |
| 5,810,874 A | 9/1998 | Lefebvre |
| 5,814,064 A | 9/1998 | Daniel et al. |
| 5,836,868 A | 11/1998 | Ressemann et al. |
| 5,843,051 A | 12/1998 | Adams et al. |
| 5,851,203 A | 12/1998 | Van Muiden |
| 5,882,329 A | 3/1999 | Patterson et al. |
| 5,895,398 A | 4/1999 | Wensel et al. |
| 5,897,567 A | 4/1999 | Ressemann et al. |
| 5,902,263 A | 5/1999 | Patterson et al. |
| 5,911,725 A | 6/1999 | Boury |
| 5,911,734 A | 6/1999 | Tsugita et al. |
| 5,935,139 A | 8/1999 | Bates |
| 5,938,645 A | 8/1999 | Gordon |
| 5,941,869 A | 8/1999 | Patterson et al. |
| 5,972,505 A | 10/1999 | Phillips et al. |
| 5,997,557 A | 12/1999 | Barbut et al. |
| 6,010,522 A | 1/2000 | Barbut et al. |
| 6,022,336 A | 2/2000 | Zadno-Azizi et al. |
| 6,066,149 A | 5/2000 | Samson et al. |
| 6,066,158 A | 5/2000 | Engleson et al. |
| 6,096,053 A | 8/2000 | Bates |
| 6,106,530 A | 8/2000 | Harada |
| 6,135,991 A | 10/2000 | Muni et al. |
| 6,142,987 A | 11/2000 | Tsugita |
| 6,146,396 A * | 11/2000 | Konya ................. A61B 17/221 606/159 |
| 6,156,005 A | 12/2000 | Theron |
| 6,159,195 A | 12/2000 | Ha et al. |
| 6,159,230 A | 12/2000 | Samuels |
| 6,160,084 A | 12/2000 | Langer et al. |
| 6,168,579 B1 | 1/2001 | Tsugita |
| 6,203,561 B1 | 3/2001 | Ramee et al. |
| 6,206,868 B1 | 3/2001 | Parodi |
| 6,238,412 B1 | 5/2001 | Dubrul et al. |
| 6,258,115 B1 | 7/2001 | Dubrul |
| 6,270,477 B1 | 8/2001 | Bagaoisan et al. |
| 6,270,513 B1 | 8/2001 | Tsugita et al. |
| 6,346,116 B1 | 2/2002 | Brooks et al. |
| 6,350,271 B1 | 2/2002 | Kurz et al. |
| 6,355,027 B1 | 3/2002 | Le et al. |
| 6,361,545 B1 | 3/2002 | Macoviak et al. |
| 6,364,894 B1 | 4/2002 | Healy et al. |
| 6,391,045 B1 | 5/2002 | Kim et al. |
| 6,402,771 B1 | 6/2002 | Palmer et al. |
| 6,425,909 B1 | 7/2002 | Dieck et al. |
| 6,454,741 B1 | 9/2002 | Muni et al. |
| 6,458,139 B1 | 10/2002 | Palmer et al. |
| 6,475,477 B1 | 11/2002 | Kohn et al. |
| 6,485,500 B1 | 11/2002 | Kokish et al. |
| 6,491,617 B1 | 12/2002 | Ogle et al. |
| 6,506,203 B1 * | 1/2003 | Boyle ..................... A61F 2/013 606/200 |
| 6,511,492 B1 | 1/2003 | Rosenbluth et al. |
| 6,514,273 B1 | 2/2003 | Voss et al. |
| 6,544,276 B1 | 4/2003 | Azizi |
| 6,569,148 B2 | 5/2003 | Bagaoisan et al. |
| 6,582,396 B1 | 6/2003 | Parodi |
| 6,592,607 B1 | 7/2003 | Palmer et al. |
| 6,596,011 B2 | 7/2003 | Johnson et al. |
| 6,610,077 B1 | 8/2003 | Hancock et al. |
| 6,620,148 B1 | 9/2003 | Tsugita |
| 6,632,236 B2 | 10/2003 | Hogendijk |
| 6,638,245 B2 | 10/2003 | Miller et al. |
| 6,641,590 B1 | 11/2003 | Palmer et al. |
| 6,645,224 B2 | 11/2003 | Gilson et al. |
| 6,660,021 B1 | 12/2003 | Palmer et al. |
| 6,663,650 B2 | 12/2003 | Sepetka et al. |
| 6,679,893 B1 | 1/2004 | Tran |
| 6,695,813 B1 | 2/2004 | Boyle et al. |
| 6,730,104 B1 | 5/2004 | Sepetka et al. |
| 6,746,468 B1 | 6/2004 | Sepetka et al. |
| 6,761,727 B1 * | 7/2004 | Ladd ................... A61B 17/221 606/108 |
| 6,805,692 B2 | 10/2004 | Muni et al. |
| 6,824,545 B2 | 11/2004 | Sepetka et al. |
| 6,878,151 B2 | 4/2005 | Carrison et al. |
| 6,890,341 B2 | 5/2005 | Dieck et al. |
| 6,911,036 B2 | 6/2005 | Douk et al. |
| 6,986,778 B2 | 1/2006 | Zando-Azizi |
| 7,029,488 B2 | 4/2006 | Schönholz et al. |
| 7,052,500 B2 | 5/2006 | Bashiri et al. |
| 7,058,456 B2 | 6/2006 | Pierce |
| 7,285,126 B2 | 10/2007 | Sepetka et al. |
| 7,344,550 B2 | 3/2008 | Carrison et al. |
| 7,534,252 B2 | 5/2009 | Sepetka et al. |
| 7,727,242 B2 | 6/2010 | Sepetka et al. |
| 7,727,243 B2 | 6/2010 | Sepetka et al. |
| 7,766,049 B2 | 8/2010 | Miller et al. |
| 7,766,921 B2 | 8/2010 | Sepetka et al. |
| 7,879,062 B2 | 2/2011 | Galdonik et al. |
| 7,931,659 B2 | 4/2011 | Bose et al. |
| 7,938,820 B2 | 5/2011 | Webster et al. |
| 7,988,705 B2 | 8/2011 | Galdonik et al. |
| 8,092,483 B2 | 1/2012 | Galdonik et al. |
| 8,118,829 B2 | 2/2012 | Carrison et al. |
| 8,262,979 B2 | 9/2012 | Anneaux et al. |
| 8,409,237 B2 | 4/2013 | Galdonik et al. |
| 8,419,786 B2 | 4/2013 | Cottone, Jr. et al. |
| 8,460,313 B2 | 6/2013 | Huffmaster |
| 8,486,104 B2 | 7/2013 | Samson et al. |
| 8,545,514 B2 | 10/2013 | Ferrera |
| 8,641,777 B2 | 2/2014 | Strauss et al. |
| 8,764,813 B2 | 7/2014 | Jantzen et al. |
| 8,784,441 B2 | 7/2014 | Rosenbluth et al. |
| 8,795,305 B2 | 8/2014 | Martin et al. |
| 8,814,892 B2 | 8/2014 | Galdonik et al. |
| 8,945,143 B2 | 2/2015 | Ferrera et al. |
| 9,067,041 B2 | 6/2015 | Watanabe et al. |
| 2002/0022859 A1 | 2/2002 | Hogendijk |
| 2002/0035347 A1 | 3/2002 | Bagaoisan et al. |
| 2002/0169472 A1 | 11/2002 | Douk et al. |
| 2003/0023263 A1 | 1/2003 | Krolik et al. |
| 2003/0040762 A1 | 2/2003 | Dorros et al. |
| 2003/0078605 A1 * | 4/2003 | Bashiri ................ A61B 17/221 606/159 |
| 2003/0135232 A1 | 7/2003 | Douk et al. |
| 2003/0153944 A1 | 8/2003 | Phung et al. |
| 2003/0163158 A1 | 8/2003 | White |

(56) References Cited

U.S. PATENT DOCUMENTS

| | | |
|---|---|---|
| 2004/0006365 A1 | 1/2004 | Brady et al. |
| 2004/0006367 A1 | 1/2004 | Johnson et al. |
| 2004/0049226 A1 | 3/2004 | Keegan et al. |
| 2004/0073243 A1 | 4/2004 | Sepetka et al. |
| 2004/0079429 A1 | 4/2004 | Miller et al. |
| 2004/0093015 A1 | 5/2004 | Ogle |
| 2004/0020611 A1 | 11/2004 | Ogle |
| 2005/0021075 A1 | 1/2005 | Bonnette et al. |
| 2005/0021152 A1 | 1/2005 | Ogle et al. |
| 2005/0033347 A1 | 2/2005 | Rauker et al. |
| 2005/0049619 A1 | 3/2005 | Sepetka et al. |
| 2005/0059995 A1 | 3/2005 | Sepetka et al. |
| 2005/0085847 A1 | 4/2005 | Galdonik et al. |
| 2005/0085848 A1 | 4/2005 | Johnson et al. |
| 2005/0085849 A1 | 4/2005 | Sepetka et al. |
| 2005/0209631 A1 | 9/2005 | Galdonik et al. |
| 2005/0277976 A1 | 12/2005 | Galdonik et al. |
| 2005/0288686 A1 | 12/2005 | Sepetka et al. |
| 2006/0058836 A1 | 3/2006 | Bose et al. |
| 2006/0189921 A1 | 8/2006 | Goldonik et al. |
| 2006/0195137 A1 | 8/2006 | Sepetka et al. |
| 2006/0200047 A1 | 9/2006 | Galdonik et al. |
| 2007/0038226 A1* | 2/2007 | Galdonik ............... A61B 17/22 606/114 |
| 2007/0060908 A1 | 3/2007 | Webster et al. |
| 2007/0060944 A1 | 3/2007 | Boldenow et al. |
| 2007/0112371 A1 | 5/2007 | Cangialosi et al. |
| 2007/0172526 A1 | 7/2007 | Galdonik et al. |
| 2007/0198028 A1* | 8/2007 | Miloslavski ........ A61B 17/221 606/127 |
| 2007/0198076 A1 | 8/2007 | Herbert et al. |
| 2007/0208371 A1 | 9/2007 | French et al. |
| 2008/0082107 A1 | 4/2008 | Miller et al. |
| 2008/0172066 A9 | 7/2008 | Galdonik et al. |
| 2008/0234706 A1 | 9/2008 | Sepetka et al. |
| 2009/0105722 A1 | 4/2009 | Fulkerson et al. |
| 2009/0198269 A1 | 8/2009 | Hannes et al. |
| 2009/0306702 A1 | 12/2009 | Miloslavski et al. |
| 2010/0204672 A1 | 8/2010 | Lockhart et al. |
| 2011/0230859 A1 | 9/2011 | Galdonik et al. |
| 2011/0251629 A1* | 10/2011 | Galdonik ............ A61B 17/221 606/159 |
| 2012/0123466 A1 | 5/2012 | Porter et al. |
| 2013/0006296 A1* | 1/2013 | McGuckin, Jr. ........ A61F 2/013 606/200 |
| 2014/0031855 A1 | 1/2014 | Clubb et al. |
| 2016/0199620 A1 | 7/2016 | Pokorney et al. |
| 2017/0143938 A1 | 5/2017 | Ogle et al. |

FOREIGN PATENT DOCUMENTS

| | | |
|---|---|---|
| JP | 2004-520893 A | 7/2004 |
| JP | 2006-094876 A | 4/2006 |
| JP | 2006-516212 A | 6/2006 |
| JP | 2009-172390 A | 8/2009 |
| WO | 95-05209 A1 | 2/1995 |
| WO | 98-34674 A1 | 8/1998 |
| WO | 98-38930 A1 | 9/1998 |
| WO | 00-76390 A2 | 12/2000 |
| WO | 01-08595 A1 | 2/2001 |
| WO | 02-02162 A2 | 1/2002 |
| WO | 02-055146 A1 | 7/2002 |
| WO | 02-085092 A2 | 10/2002 |
| WO | 03-000334 A1 | 1/2003 |
| WO | 2004-062513 A1 | 7/2004 |
| WO | 2005-000130 A1 | 1/2005 |
| WO | 2006-031410 A2 | 3/2006 |
| WO | 2007-117645 A2 | 10/2007 |
| WO | 2009-014723 A1 | 1/2009 |
| WO | 2009-086154 | 7/2009 |
| WO | 2010-010545 A1 | 1/2010 |

OTHER PUBLICATIONS

Feldman, "Transcatheter Aspiration of a Thrombus in an Aortocoronary Saphenous Vein Graft," Am. J. Cardiol. 60 (4):379-380 (1987).

Nakagawa et al, "A Retrievable Nitinol Vena Cava Filter: Experimental and Initial Clinical Results," Journal of Vascular and Interventional Radiology 5:507-512 (1994).

Product brochure for Merci Retrieval System®, produced by Concentric Medical, Inc. 2010 (2 Pages).

Office action for co-pending Japanese Patent Application No. 2013-505050 dated Dec. 16, 2014 (7 pages with translation).

Office action for co-pending Japanese Patent Application No. 2015-177832 dated Aug. 2, 2016 (4 pages).

European Search Report and Written Opinion from co-pending application No. 1684291.3-1113/3344184, from PCT/US2016/49723, dated Apr. 15, 2019.

\* cited by examiner

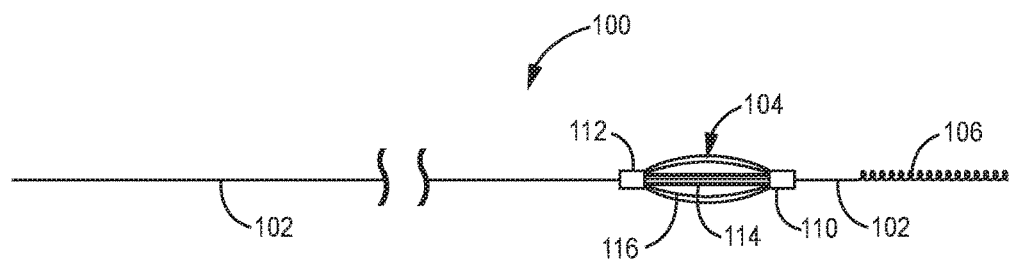
FIG. 1
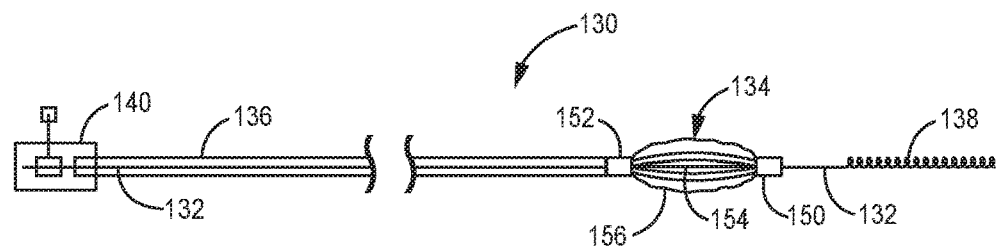
FIG. 2
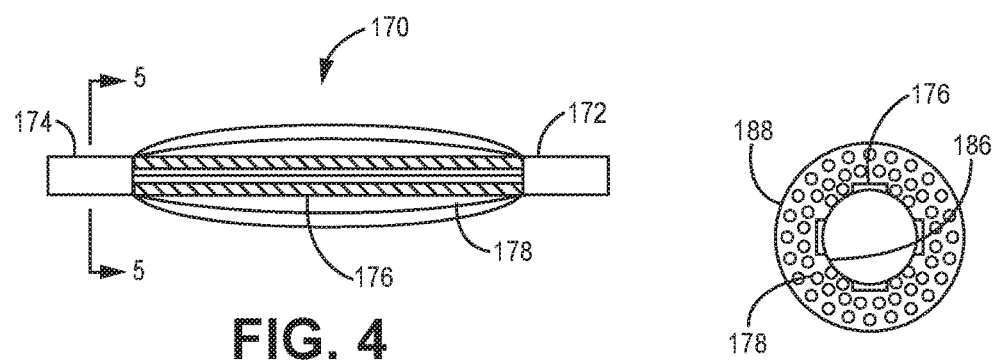
FIG. 4
FIG. 5
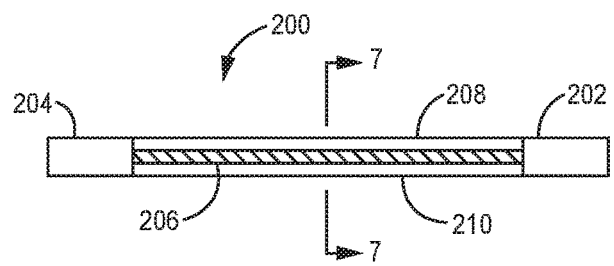
FIG. 6
FIG. 7
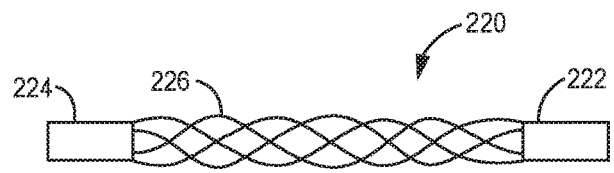
FIG. 10

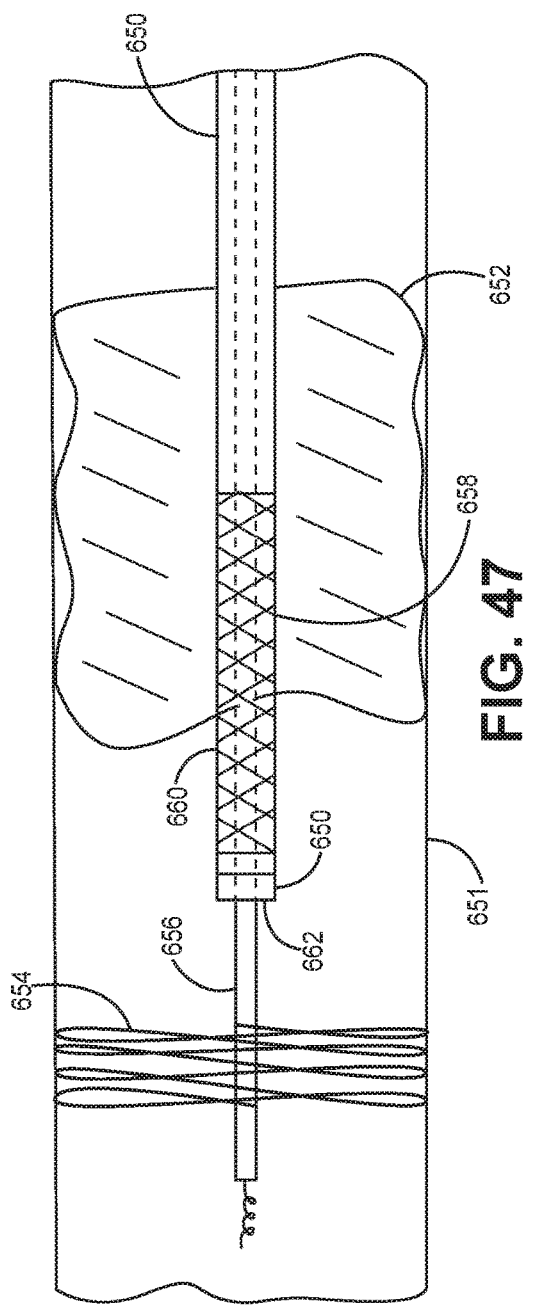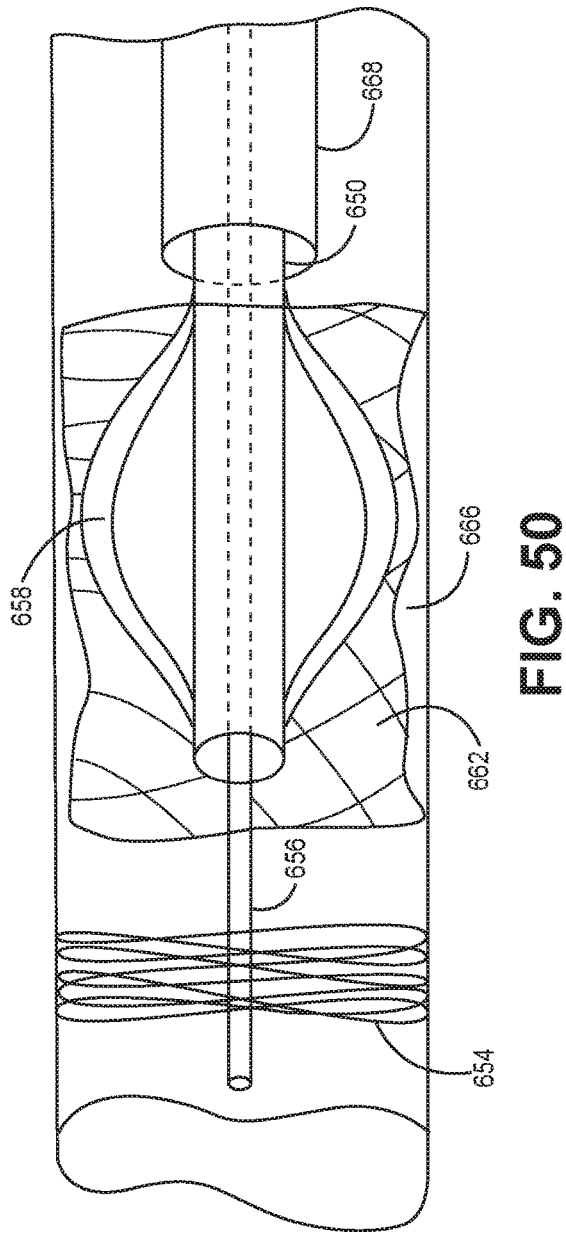

THROMBECTOMY DEVICES AND TREATMENT OF ACUTE ISCHEMIC STROKE WITH THROMBUS ENGAGEMENT

CROSS REFERENCE TO RELATED APPLICATIONS

This application claims priority to U.S. provisional patent application 62/212,773 filed Sep. 1, 2015 to Ogle et al, entitled "Methods and Devices for Clot Removal in Cerebral Vessels," incorporated herein by reference.

FIELD OF THE INVENTION

The invention relates to treatment systems and component devices designed for the engagement and removal of thrombus, especially from cerebral arteries associated with acute ischemic strokes. The invention further relates to method of performing thrombectomy procedures for the alleviation of ischemic stroke events.

BACKGROUND OF THE INVENTION

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction. To reduce the effects of the cut off in blood supply to the tissue, time is an important factor. In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries.

SUMMARY OF THE INVENTION

In a first aspect, the invention pertains to a filter device comprising a guide structure, an anchor secured at a fixed location on the guide structure having a central axis, a slide positioned over the guide structure, an a filter cartridge secured on one end to the anchor and on the other end to the slide. In some embodiments, the filter cartridge can comprise a plurality of polymer fibers in a bundle when in an un-deployed configuration, and one or more metal elements radially below relative to the central axis the bundle of polymer fibers secured around the guide structure, wherein the metal elements have a deployed configuration with the slide approaching closer to the anchor with the metal elements forming a curved structure extending radially outward, and wherein the device has an un-deployed low profile configuration and an unconstrained deployed configuration with the furthest radial extent of the metal elements being below a mat of fibers.

In a further aspect, the invention pertains to a stent retriever comprising a tether and a self-extending structure extending in a distal direction from the tether, the self-extending structure comprising an open metal frame that extends without constraint into a generally cylindrical shape with a slit along the length of the cylinder and a polymer cover extending around and adhered to the exterior of the open metal frame. In some embodiments, the polymer cover has a slit along the slit of the metal frame.

In other aspects, the invention pertains to a treatment device comprising a microcatheter, an extendable atherectomy component secured to the outer surface of the microcatheter, and a sheath slideable over the exterior of the microcatheter. The microcatheter can have an outer diameter from about 1 Fr to about 3.5 Fr and an inner lumen extending along the length of the catheter. The extendable atherectomy component can be mounted on the exterior of the microcatheter at or near the distal end of the microcatheter. The sheath can extend over the extendable atherectomy component in a low profile delivery configuration and has a configuration moved in a proximal direction over the microcatheter with the extendable atherectomy component unconstrained with respect to extend radially outward.

In additional aspects, the invention pertains to a treatment system comprising a guide structure, an atherectomy component connected to the guide structure, a microcatheter comprising a lumen through which the guide structure can slidably move, and a stent mounted on the exterior of the microcatheter near the distal end of the microcatheter.

Moreover, the invention pertains to a method for the removal of obstructive material from a blood vessel, the method comprising:

deploying a filter device mounted on a guide structure from the lumen of a microcatheter in a blood vessel downstream from an obstruction;

deploying a stent and a atherectomy component in the blood vessel proximal to the position of the deployed embolic protection device using a microcatheter wherein either the stent or the atherectomy device are deployed from the exterior of the microcatheter and the other component is deployed from the interior of the microcatheter; and performing an atherectomy procedure to disrupt thrombus for removal at the site of the deployed stent with the deployed filter device in place while suction is applied from a proximal position with an aspiration catheter.

BRIEF DESCRIPTION OF THE DRAWINGS

FIG. 1 is a side view of an embodiment of a fiber based guide structure in an un-deployed delivery configuration with a self-extending filter device.

FIG. 2 is a side view of an alternative embodiment of a fiber based filter element in an un-deployed delivery configuration with an overtube configured as an actuation element.

FIG. 4 is a side view of a filter cartridge with polymer fibers and metal elements shown in an un-deployed low profile configuration.

FIG. 5 is a sectional view of an attachment element of the filter cartridge of FIG. 4 taken along line 5-5.

FIG. 6 is a side view of a filter cartridge with polymer fibers removed to expose unwoven metal elements in an un-deployed low profile configuration.

FIG. 7 is a sectional view of the metal elements of FIG. 6 taken along lines 7-7.

FIG. 10 is a side view of a filter cartridge with braided metal elements in an un-deployed low profile configuration with polymer fibers removed to show the metal elements.

FIG. 47 is a fragmentary side view of a blood vessel with a microcatheter and a fiber based filter on a guide structure extending past a clot in the vessel in which the microcatheter has a first treatment structure mounted on the exterior of the microcatheter covered with a sheath and a second treatment structure within its lumen.

FIG. 50 is a fragmentary side view of the vessel of FIG. 49 with a stent retriever deployed within the stent lumen.

DETAILED DESCRIPTION OF THE INVENTION

Figure 3:
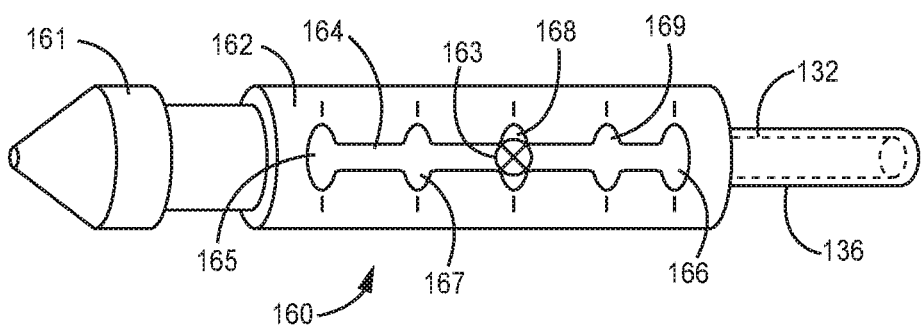
FIG. 3 is a side perspective view of a representative embodiment of an actuation tool configured as a pull element with intermediate looking positions between the limits of the range of motion.

Treatment systems are described for the engagement and at least partial removal of clots, i.e., thrombus, in which components of the treatment systems are designed to present low risk to vessel walls during the procedure, especially useful within cerebral arteries during acute ischemic stroke events. In some embodiments, the treatment systems comprise a fiber based filter structure to provide some embolic protection and a suction catheter to remove thrombus. The filter structure may or may not be used to provide direct engagement with the clot and can catch at least some emboli that may dislodge from the clot. The filter structure can comprise metal elements, which may or may not be self-extending, and polymer fibers configured to extend surrounding the metal elements with the polymer fibers providing a cushion protecting the vessel walls in addition to forming a fiber mat with filtration capability. Also, a stent retriever design is described with a tether extending gradually into a cut cylinder with an open frame that can be covered with a cover, e.g., a porous material. A polymer cover on the exterior of a stent retriever can provide additional cushion against the vessel wall, and in some embodiments an enclosed distal end with a porous material can simultaneously provide embolic protection. In some embodiments, the procedure comprises deployment of a stent at the location of the thrombus, such that the stent can be used to provide protection to the vessel wall during subsequent steps to remove thrombus. An atherectomy device, e.g., a stent retriever, with a selected amount of abrasive capability may be used to remove thrombus within the interior of the stent with protection to the vessel wall provided by the stent. Improved delivery systems are described to provide for delivery of a stent and an atherectomy device from the microcatheter, with one of the components optionally delivered from the surface of the microcatheter. The treatment systems described can be used to provide real time treatment for the relief of an acute ischemic stroke event.

To reduce the clinical effects of a clot within a cerebral artery, the clot or portion thereof can be removed, and it is correspondingly desirable to keep the time for relieving vessel occlusion short. For convenience, as used herein, all arteries downstream from the interior carotid arteries are referred to as a cerebral artery, and generally in the art blood vessels in the head can be referred to as the neurovasculature. The process of removal of a clot from the cerebral arteries can pose a challenge of tracking a device to the clot and physically engaging the clot to remove it. Any portions of the clot that remains in the vessel or breaks off from the original clot can eventually flow downstream to block a smaller vessel with associated harm to the patient. The placement of a filter device within a cerebral artery poses significant challenges due to the circuitous path through the vessels and the small size of the vessels, and useful devices for these purposes are described based on a combination of metal elements and polymer fibers. As used herein, clot and thrombus are used interchangeably unless otherwise indicated. The terms proximal and distal are used as conventional in the catheter art with distal meaning the end inserted into the patient and the direction away from the entry point into the patient, and proximal meaning the opposite end and the direction toward the entry point into the patient.

Due to the circuitous nature of the cerebral arteries, the devices intended for placement up the cerebral arteries are designed for a high degree of flexibility and maneuverability. A guidewire can be used to provide initial access to the location of the procedure, generally with the distal end of the guidewire extending past the thrombus. Also, a guide catheter can be placed in the patient generally with the distal end of the guide catheter in a carotid artery. Various therapeutic devices can be delivered over the guidewire and/or through the guide catheter. A guidewire may be removed at some point of the procedure. A filter/fiber based structure can be mounted on a guide structure and can be put in place of the guidewire while potentially providing for assistance with device delivery.

A desirable fiber based filter can comprise metal elements, which may be self-expanding spring metal, with a bundle of polymer fibers that can be mounted as a cartridge. The metal elements can provide mechanical strength to facilitate engagement of thrombus. The metal elements can also support the filtration matrix in view of the limited polymer fibers deliverable into a small vessel in a single cartridge. The metal elements generally are placed radially below a bundle of fibers, which comprise polymer fibers and optionally some thin metal wires. The metal elements generally can be designed to curve upon deployment so that the radial extend of the deployed metal elements can be significantly less than the polymer fibers, which can be supplemented with thin metal wires. The metal elements forming the understructure can be formed from self extending spring metal to provide self actuation, although in alternative embodiments an overtube, such as a flexible polymer overtube, can extend proximally from the fiber bundle to function as an actuation tool. The fibers bundle can provide a cushion between the vessel walls and the metal elements as well as forming a filtration matrix. The metal elements and the fibers can be joined within a cartridge generally with the metal elements positioned below the polymer fibers with supports holding the ends of the metal elements and fibers.

Fiber based embolic protection devices were developed to provide protection during procedures in the vasculature. See, for example, U.S. Pat. No. 7,879,062 to Galdonik et al., entitled "Fiber Based Embolism Protection Device," and U.S. Pat. No. 7,988,705 to Galdonik et al., entitled "Steerable Device Having a Corewire Within a Tube and Combination With a Functional Medical Component," both of which are incorporated herein by reference. The potential usefulness of fiber based embolic protection devices for thrombectomy or embolectomy procedures is described in published U.S. patent application 2008/0172066 to Galdonik et al., entitled "Embolectomy Procedures With a Device Comprising a Polymer and Devices with Polymer Matrices and Supports," incorporated herein by reference. These devices can comprise a fiber mat formed of the fibers in a deployed configuration such that the fiber mat has the structure of a three dimensional filtration matrix. The three dimensional filtration matrix comprises effective pores with a distribution of sizes within the matrix. The pores with various sizes inside the matrix provide complex flow passages through the fiber mat to allow blood to pass through while effective retain emboli of various sizes. In some embodiments, the fibers are configured to be a non-woven bundle. Even after the deployment and formation of the fiber mat, the fibers form an unwoven fiber mat.

Based on the challenges of procedures in the neurovasculature, modified fiber based devices were developed with consideration of the mechanical challenges. These modified devices are described in U.S. Pat. No. 8,814,892 to Galdonik et al. (hereinafter the '892 patent), entitled "Embolectomy Devices and Methods for the Treatment of Acute Ischemic Stroke Condition," incorporated herein by reference. The present fiber based devices involve additional design improvements that reduce procedure steps while providing desired functionality and good performance. In some embodiments, a self-extending fiber based structure can be extended within the thrombus to embed in the thrombus, although in further embodiments, the fiber based filter device is deployed distal to the thrombus.

Fiber based filter structures generally are secured to a guide structure and generally have a lower profile initial configuration and a larger profile extended configuration. The guide structure can be a guidewire configured to support the filter, a corewire with an overtube that provides actuation function with respect to the filter, or similar structures possibly with additional features to the structure. Embodiments with a corewire and overtube can comprise a torque coupler as described below in some embodiments. In some of the procedures described herein, the fiber based filter, supported on a guide structure can be delivered through the lumen of a microcatheter, which can facilitate guiding of the filter past the clot.

As described further below, suction provided by an aspiration catheter can be a significant tool for thrombus removal. The filter device can be used in conjunction with a suction catheter to pull the clot from the distal side while suction draws the clot from the proximal side. An alternative to or as an addition to relying on suction and pulling of a clot to remove the clot from the vessel, mechanical fragmentation of the clot can be used to facilitate removal of the thrombus. The systems described herein can be designed and implemented to provide protection for the vessel wall during the process. The systems described herein can use abrasive elements, e.g., atherectomy devices, to macerate the thrombus for removal. As used herein, atherectomy devices refer to any component that can abrade thrombus, which may involve application of motorized forces or mechanical forces applied manually by a user. The term "stent retriever" which has evolved in the art even though the devices may or may not particularly resemble components of a stent, is used herein to refer to components using manual forces applied by a user to abrade the thrombus. Stent retrievers generally are described, for example, in U.S. Pat. No. 8,945,143B2 to Ferrera et al., entitled "Expandable Tip Assembly for Thrombus Management," and published U.S. patent application 2012/0123466A1 to Porter et al., entitled "Axially Variable Radial Pressure Cages for Clot Capture," both of which are incorporated herein by reference.

The use of stent retrievers or other atherectomy devices can result in damage to vessel walls. Stent retriever designs are described herein can reduce potential damage through the introduction of radial elasticity and/or through the use of a polymer cover that can cushion the metal frame against the vessel wall. In some treatment systems described herein, a stent can be deployed first to protect the vessel wall prior to the use of an atherectomy device.

Stent retriever designs are described that use a tether from which a frame unfurrows. A gradually growing frame arch can extend in a distal direction from the tether as part of a frame that in an extended configuration can have a cut cylindrical shape. A cut along the length of the device, which may or may not be straight in an axial sense, can provide desirable radial elasticity. The edges can fold within themselves when deployed in a vessel to provide constraints on the force extended against the vessel wall, so that the stent can better accommodate a polymer cover attached to the surface with reduced stress from the expanding metal frame.

A polymer cover and optionally a liner can be placed on the outside (and optionally inside) of a stent retriever. A polymer cover softens the metal elements of the frame to reduce risk of damage to the vessel wall. In some embodiments, the cover and liner if present can be porous so that blood profusion can take place through the cover. The cover or other porous material may or may not enclose the distal end of the device. If the cover or additional material covers the distal end of the device and further extends in a distal direction from the cylindrical frame, the porous filter material can function to trap emboli, and in such embodiments, a separate filter may or may not be used depending on the design of the structure. In some embodiments, the cover can extend distally from the metal frame with the slit extending along at least part of the distal direction such that a stent retriever constrained in a vessel can fold the material closed as an envelope. In some embodiments, a porous filter material can be attached as an enclosure of the distal end. If the distal end of the device is open, a filter can be used distal to provide embolic protection during the procedure.

Efficient systems are described for the deployment of stents and stent retrievers in association with a microcatheter and their effective use for thrombus removal. In particular, a stent retriever can be mounted on the exterior of a microcatheter to reduce the number of steps needed for the protected atherectomy procedure, while a stent can be delivered from the interior of the microcatheter. In some embodiments, a stent can be delivered from the exterior of a microcatheter and a stent retriever can be delivered from the interior of the microcatheter.

For some embodiments herein using atherectomy devices, it can be desirable to use a fiber based filter deployed distal from the treatment site to catch some or all emboli released by the abrasive interaction with the thrombus as the clot is removed. The desirable filter designs described herein can be used or other designs from the '892 patent can be used. After use of an atherectomy device, the filter can engage any remaining thrombus as it is removed in a deployed configuration to facilitate removal of any remaining portions of thrombus in the vessel. As noted above, the fiber based filters can be used to engage the thrombus for removal even without the use of an atherectomy device.

Suction can be applied at appropriate portions of the procedures to capture and remove the clot or portions thereof with the assistance and protection provided by the other elements. Aspiration catheters have been developed that are particularly suitable for delivery into cerebral arteries to provide strong suction. These catheters are described further below. The aspiration catheter can provide for removal of the clot or fragments thereof during the progression of the procedure while a fiber based filter can provide protection from escape of emboli as a boundary on the back end of the procedure.

The devices described herein provide for streamlined procedures for the efficient performance of thrombectomy procedures, which can be particularly effective for the treatment of acute stroke events. The components are designed to reduce any trauma to the vessel wall resulting from the procedure. Protection against damage to the vessel wall can be provided by the polymer fibers surrounding metal elements of the filter and by a stent that can limit the interaction of an atherectomy device with the vessel wall. Delivery of components in association with a microcatheter can reduce procedure times and complexity while providing effective components and protection to vessel walls. The components can be packaged in sterile packing as individual components or together as systems as desired along with instructions according to regulatory guidelines.

Fiber Based Filter

The fiber based filters provide a convenient design that protects the vessel wall, has desirable mechanical properties and is suitable for efficient and rapid thrombectomy procedures. The devices are supported on a wire structure with an anchor that holds one secured end of extendable elements and a slide element that holds the other secured end of the extendable elements. The extendable elements can be grouped in a bundle and comprise metal, such as spring metal elements and polymer fibers. Generally, the metal elements are placed under at least some of the polymer fibers so that the polymer fibers form a cushion around the metal elements. The metal elements can be designed to form curved structure upon extension such that their radial extent is limited upon deployment. In an un-deployed configuration the metal elements and polymer fibers can be stretched to reduce the radial profile the filter cartridge for deployment. The diameter of the un-deployed element can be suitable for sliding within a microcatheter lumen.

The filter cartridge can be designed to balance a range of factors with design constraints for delivery into small circuitous vessels. As noted in the '892 patent, the narrowness of the vessels constrains the numbers of fibers within a bundle that can be conveniently deployed. Various embodiments are described in the '892 patent for the delivery of multiple bundles of fibers to make up for this physical constraint. While those embodiments may be desirable for certain application, the present fiber structures with a single fiber bundle are designed for ease of use by physicians, rapid deployment and functionality with respect to mechanical strength for engaging a clot. Whether or not a self extending design is used, the fiber cartridges have metal elements under the polymer fibers designed to deploy to a smaller radial dimension than the extended polymer fibers. With this design, the polymer fibers provide a cushion between the metal elements and the vessel wall. The device can be designed to expand out to the vessel wall and maintain contact as the device is pulled through the vessel. With the limited number of fibers available in the single filter cartridge, the metal provides significant mechanical stabilization for the engagement of the clot or fragments thereof. A web coating over the fiber cartridge can also provide desirable properties to the deployed filter. The mechanical stabilization also facilitated capture of any clot fragments, i.e., emboli, generated during the procedure by the fiber matrix that is formed upon deployment of the device.

Referring to FIG. 1, an embodiment of a filter device 100 is shown with a self-extending filter cartridge. Filter device 100 comprises guide structure 102, filter cartridge 104 and optional distal coil 106. Guide structure 102 can be a flexible wire, which can be metal or polymer. Optional distal coil 106 can be formed from metal or other suitable flexible material. In this embodiment, filter cartridge 104 comprises distal anchor 110, proximal slide 112, metal elements 114, and fibers 116. Fibers 116 comprise polymer fiber and optionally thin metal wires, such as tungsten wires, that deploy with the polymer fibers. Generally, metal wires that deploy with the polymer fibers have a smaller circumference than metal elements 114. Details of embodiments for filter cartridge 104 are described further below.

Referring to FIG. 2, an alternative embodiment of a filter device 130 is depicted, which generally is not self actuating. Filter device 130 comprises guide structure 132, filter cartridge 134, polymer overtube 136, optional distal coil 138 and actuation tool 140. Guide structure 132 and optional distal coil 138 can have features as described above for guide structure 102 and optional distal coil 106. Filter cartridge 134 comprises distal anchor 150, proximal support 152, metal elements 154, and fibers 156. Fibers 156 comprise polymer fiber and optionally thin metal wires, such as tungsten wires, that deploy with the polymer fibers. Generally, metal wires that deploy with the polymer fibers have a smaller circumference than metal elements 154. Proximal support 152 differs from proximal slide 112 by the direct or indirect attachment of polymer overtube to proximal support so that proximal support 152 cannot slide without movement of polymer overtube 136. Polymer overtube 136 can attach to proximal support 152 through any reasonable design, such as abutting each other with a brace or wrap, such as shrink wrap, securing both elements with polymer overtube 136 extending over at least a portion of proximal support 152 with an adhesive sealing the elements, or other suitable approach using mechanical and/or adhesive bonding. Remaining details of appropriate embodiments of filter cartridge 134 are provided below.

To facilitate deployment of the actuated embodiment in FIG. 2, actuation tool 140 can be used to assist a medical professional to move guide structure 132 relative to polymer overtube 136 an appropriate amount while reducing the chance of bending or kinking the thin elements. Various tools have been developed for a similar actuation purpose for fiber based devices designed for use in vessels in other portions of the body. Referring to FIG. 3, an embodiment of an actuation tool is shown with a ratchet style pull element 160. Pull element 160 comprises slide 161 and body 162. Button 163 is attached to slide 161. Body 162 has a slot 164 that constrains the position of button 163. In this embodiment, slot 164 has two end stop points 165, 166 and three intermediate stop points 167, 168, 169. The operator can select the particular stop point to position guide structure 132 relative to overtube 136 at one of the end points of its range of motion or at an intermediate stop point. Friction based ratchet structures can be similarly used. In other embodiments, one intermediate stop points, two intermediate stop points, four intermediate stop points, five intermediate stop points, ten intermediate stop points, 20 intermediate stop points, or any number in between can be used as an alternative to the three intermediate stop points shown in FIG. 3 based on the disclosure herein. Additional embodiments of actuation tools that can be adapted for the present devices are shown, for example, in the '892 patent.

An isolated filter cartridge is shown in FIG. 4. Filter cartridge 170 comprises distal support 172, proximal support 174, metal elements 176, and polymer fibers 178. Distal support 172 and proximal support 174 can comprise an inner tube 186 and a cover 188 with polymer fibers 178 and metal elements 176 (optionally for the distal support) fixed between them, as shown in the enlarged schematic sectional view in FIG. 5. Distal support 172 can be formed without an inner polymer tube by securing the metal elements and/or polymer fibers against the guide structure, but the use of the inner polymer tube can provide production convenience for this element. Inner tube 186 can be formed from polyimide, PEEK, or other suitable medical grade polymer or metal. Cover 188 can be a metal foil crimped over the structure, polymer shrink wrap, adhesive, combinations thereof or the like.

Figure 8:
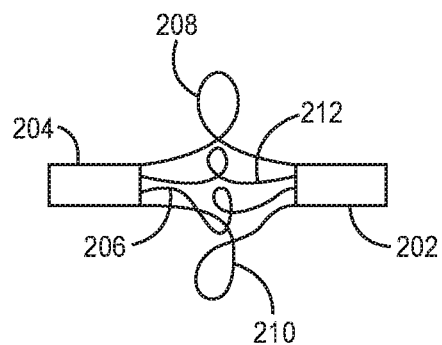
FIG. 8 is a schematic side view of a deployed filter cartridge with four curved metal elements and with polymer fibers removed to show the metal elements.
Figure 9:
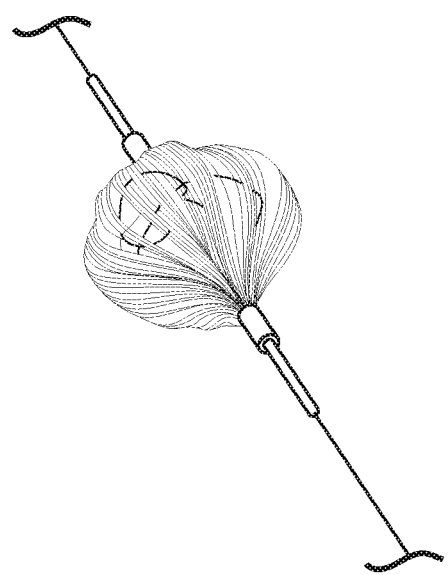
FIG. 9 is a photograph of a prototype of a filter cartridge with three metal elements extended into pedal shapes and surrounded by bent polymer fibers.
Figure 11:
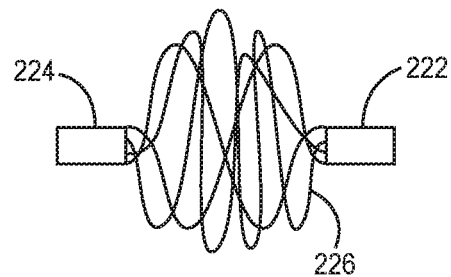
FIG. 11 is a schematic side view of a fiber cartridge with braided metal elements in a deployed extended configuration.

Two embodiments of a filter cartridge are shown in FIGS. 6 and 10 with the polymer fibers removed to show embodiments of the metal structures unobstructed. Referring to FIGS. 6 and 7, depicted filter cartridge 200 comprises distal support structure 202, proximal support structure 204 and four unwoven metal elements 206, 208, 210, 212 designed to extend into a curved structure. A section view of filter cartridge 200 in FIG. 7 shows metal elements 206, 208, 210, 212 around an open inner space. A view of the extended device is shown in FIG. 8. The metal elements extend into petal shaped features that limit the radial extension relative to the total length of the element. A picture of a prototype device is shown in FIG. 9 in which three extended metal elements are nicely cushioned by the polymer fibers that extend radially outward to the extent provided by the constrained ends of the fibers. While FIGS. 6-8 depict 4 metal elements and FIG. 9 depicts 3 metal elements, a greater or lesser number of metal elements can be used, such as two metal elements, five metal elements, six metal elements, seven metal elements, eight metal elements or greater than 8 metal elements.

Figure 12:
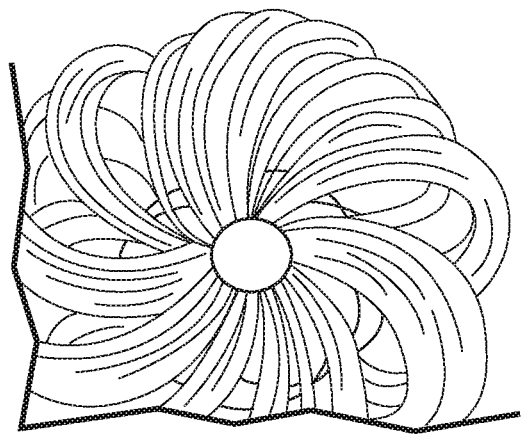
FIG. 12 is a photograph of a prototype of a filter cartridge with braised metal elements surrounded by bent polymer fibers.

Referring to FIG. 10, depicted filter cartridge 220 comprises distal support 222, proximal support 224, and braided metal element 226. The braided metal elements twist around the axis of the device as well as extend laterally along the length. The braided structure extends into a curved surface in which has limited radial extent relative to the length of the individual wires in the braided structure due to twisting around the axis of the device. Overlapping portions of the braid can be welded together reminiscent of a stent structure, but since the ends are fastened at both ends, less strain is placed on the structure at deployment if the braids are free to slide past each other when deploying. The number of metal strands woven together can be based on the physical constraints of the cartridge size, and can generally be 3, 4, 5, 6, 7, 8 or more than eight strands in the braid. Referring to FIG. 1I, the extended braided metal element is depicted in an extended structure. A prototype is shown in FIG. 12 in which the polymer fibers form a cushion over the extended metal element.

Figure 13:
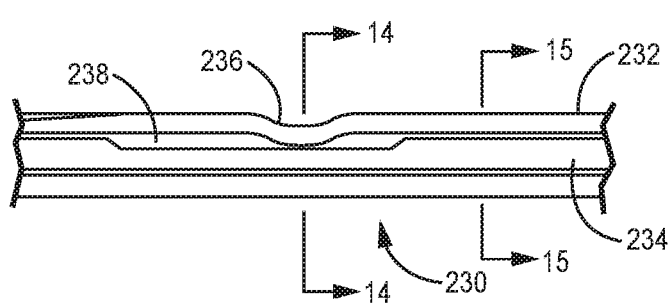
FIG. 13 is a fragmentary, expanded sectional side view of a torque coupler embodiment with a notch in a corewire engaged by an indentation in an overtube.
Figure 14:
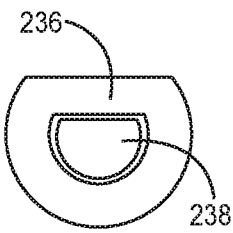
FIG. 14 is a sectional view of the torque coupler of FIG. 13 taken along line 14-14.
Figure 15:
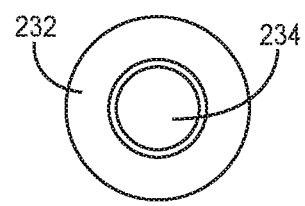
FIG. 15 is a sectional view of the device of FIG. 13 taken along line 15-15.

As described further below, the present devices are designed in some embodiments for delivery through a microcatheter, as essentially a delivery sheath. For these embodiments, it is desirable for the majority of the device to be highly flexible, but it is not necessarily significant if the device can be tracked as a guide wire through the vasculature. Thus, for some embodiments, it may not be significant to be able to transmit torque from the proximal end to the distal end to rotate the tip of the device. For embodiments as in FIG. 2 with an overtube that can be polymer or metal, torque couplers can be designed into the devices to facilitate transfer of torque from the overtube to the guide structure. An embodiment of a torque coupler is shown in FIG. 13. Torque coupler 230 comprises corresponding structural features in overtube 232 and guide structure 234 that interface to form the torque coupler. Referring to sectional views in FIGS. 14 and 15, overtube 232 comprises notch 236 that forms a portion of the torque coupler 230. Referring to FIGS. 13 and 14, guide structure 234 has a flattened key portion 238 that forms a portion of torque coupler 230. Key portion 238 generally can have a length of about 5 mm to about 5 centimeters along the wire. Generally, a torque couple may be placed within the distal quarter of the length of the device, although a device can comprise a plurality of torque couplers, which generally would be spaced apart along the length of the device generally with one along the distal quarter of the device. Torque couplers are described further in U.S. Pat. No. 7,988,705 to Galdonik et al., entitled "Steerable Device Having a Corewire Within a Tube and Combination with a Functional Medical Component," incorporated herein by reference.

The length of filter device 100 or 130 can generally be selected for the particular procedure design. For example, for entry into the vasculature in the femoral artery for guiding into the cerebral arteries, the overtube generally would have a length from about 190 cm (63 inches) to about 300 cm (106 inches), although shorter lengths such as 30 cm to 190 cm may be suitable for other entry vessels. Guide structure 102 and 132 can have a diameter from about 0.001 inches to about 0.01 inches, in further embodiment from about 0.002 inches to about 0.007 inches and in additional embodiments from about 0.003 inches to about 0.006 inches. The cross section of polymer overtube 136 can be characterized by an inner diameter and an outer diameter. The inner diameter general ranges from about 0.001 inches to about 0.01 inches, in further embodiment from about 04003 inches to about 0.008 inches and in additional embodiments from about 0.005 inches to about 0.007 inches. The outer diameter generally ranges from about 0.04 inches to about 0.009 inches, in further embodiments from about 0.03 inches to about 0.010 inches, in additional embodiments from about 0.02 inches to about 0.011 inches and in other embodiments from about 0.015 inches to about 0.013 inches, with standard guidewire outer diameters being about 0.014 inches. Guide structure 132 can have an outer diameter just slightly less than the inner diameter of the tube by about 0.001 inches to about 0.003 inches. A person of ordinary skill in the art will recognize that additional ranges within the explicit ranges for the diameters are contemplated and are within the present disclosure.

In general, guide structures 102, 132 can be formed from one or more of various materials, such as polymers, metals and combinations thereof, although metals can provide convenient balance of strength, flexibility and deliverability to a target location in a cerebral vessel. Suitable materials are generally biocompatible in that they are non-toxic, non-carcinogenic and blood compatible and do not induce hemolysis or a significant immunological response. Suitable biocompatible metals include, for example, titanium, cobalt, stainless steel, nickel, iron alloys, cobalt alloys, such as Elgiloy®, a cobalt-chromium-nickel alloy, MP35N, a nickel-cobalt-chromium-molybdenum alloy, and Nitinol®, a nickel-titanium alloy. Some of these metals are suitable for use as shape memory metals in which a particular shape is designed into the metal element upon formation, and the elements can be distorted to another shape for delivery and later allowed to resume its predesigned shape. Shape memory metals can be used for self actuation. Suitable polymers, such as for the polymer fibers, include, for example, polyamides (e.g., nylon), polyesters (e.g., polyethylene terephthalate), polyacetals/polyketals, polyimide, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, polyether ether ketones (PEEK), ethylene vinyl acetates, polysulfones, nitrocelluloses, similar copolymers and mixtures thereof. In the embodiments of the device of FIG. 2, polymer overtube 136 can be formed from, for example, polyimides, PEEK or the like. In alternative embodiments, polymer overtube 136 can be replaced with a metal tube for the actuation of the filter cartridges described herein.

In some embodiments, the surface of guide structures 102, 132, the inner surface of polymer overtube 136 or equivalent element, the outer surface of the polymer overtube 136 or equivalent element, portions thereof or combinations thereof is coated with a friction reducing agent. Suitable friction reducing agents include, for example, suitable polymers, such as polytetrafluoroethylene, i.e., Teflon® or a polymer coating such as parylene.

The fibers of the fiber bundle can be approximately uniformly fixed around a central axis of the filter cartridge in the un-deployed configuration. The approximate cylindrical symmetry of the bundle around the guide structure in the un-deployed configuration facilitates the deployment of the fiber bundle into a filter matrix that has a desirable configuration across the blood vessel upon deployment. The fibers can be selected to have desired mechanical properties in the vessel. In general, the fibers should be flexible so that the fibers can be delivered into the vessel and such that the fibers do not injure the vessel wall. Fibers can be formed from a radiopaque material, as described in published U.S. patent application 2007/0172526A to Galdonik et al., entitled "Radiopaque Fibers and Filtration Matrices," incorporated herein by reference.

It is desirable for the device to have radiopaque markers for visualization of the device during treatment procedures in real time. Visualization can be useful to confirm proper placement of the device relative to the treatment site. The metal elements within the fiber can provide some visualization. Additionally or alternatively, radiopaque marker bands can be used to mark specific positions on the device. Radiopacity can be achieved with the addition of metal structures comprising metals, such as platinum-iridium or platinum-tungsten or through radio-pacifiers, such as barium sulfate, bismuth trioxide, bismuth subcarbonate, powdered tungsten, powdered tantalum or the like, added to a polymer. For example, radiopaque materials can be added to the support elements binding the fiber ends.

The fibers can have a suitable cross sectional shape to provide desired mechanical properties. In some embodiments, the fibers can have a circular cross section, oval cross section or other convenient shape. In some embodiments, surface capillary polymer fibers can be used, which have one or more surface capillaries extending along the length of the fiber. The use of surface capillary fibers for three dimensional filtration matrices for embolic protection devices is described further in published U.S patent application 2005/0209631A to Galdonik et al., entitled "Steerable Device Having a Corewire Within a Tube and Combination With a Functional Medical Component," incorporated herein by reference.

A particular device can comprise one or more types of fibers, such as polymer fibers and some thin metal wires. In some embodiment, the same bundle of fibers can comprise one or more types of fibers to provide desired mechanical and filtration properties. The thickness of the fibers can be selected appropriately for the particular use of the fiber. Fiber thickness can be measures in several ways. The radius of the fiber can be roughly estimated from the assumption of a circular cross section. Alternatively, one can define an average diameter by taking an average cross section and then averaging the length of segments through the center of the cross section that intersect the circumference of the cross section. Also, calipers can be used to measure thickness, which can be averaged to obtain a value of the diameter. These various approaches at estimating the radius or diameter generally give values of roughly the same magnitude.

Also, in the fiber field, a pragmatic way has been developed to characterize fiber thickness, especially polymer fibers, without the need to resort to magnification of the fibers. Thus, fiber thickness can be measured in units of denier. Deniers correspond to the number of grams per 9,000 meters of yarn with a larger value corresponding to a thicker fiber. In some embodiments, suitable fibers have diameters from 1 micron to about 75 microns, in further embodiments from about 2.5 microns to about 50 microns, and in additional embodiments from about 5 microns to about 40 microns. As measured in denier, suitable fibers can have sizes ranging from about 0.02 denier to about 50 denier in size, in additional embodiments from about 0.05 denier to about 30 denier, in some embodiments from about 0.1 denier to about 20 denier, in other embodiments from about 0.2 denier to about 15 denier and in further embodiments from about 0.4 denier to about 10 denier. The number of fibers can be selected based on the diameters with the constraint of the inner diameter of a delivery catheter, such as a microcatheter. For the fiber based filter structure, a bundle of fibers generally comprises from about 25 to about 500 polymer fibers, in further embodiments from about 30 to about 400 polymer fibers and in additional embodiments from about 35 to about 300 polymer fibers. Generally, if the fibers or stands of both polymer and metal composition further comprise thin metal wires, from 1 to 10 percent of the fibers/strands can be thin metal wires. The diameter of the thin metal wires generally are from about 0.0001 inches (2.4 microns) to about 0.002 inches (48 microns) and in further embodiments from about 0.0002 inches (4.8 microns) to about 0.001 inches (24 microns). A person of ordinary skill in the art will recognize that additional ranges of fiber (polymer and/or metal) thickness in diameter measurements or in denier and fiber numbers (polymer and/or metal) are contemplated and are within the present disclosure.

The lengths of the fibers should be selected such that the deployed fibers fill the vessel lumen. Thus, if the fibers are bent in the deployed configuration, the fibers should have lengths greater than a factor of 2 larger than the vessel radius. The devices can be supplied with different sizes available for selected deployment based on the size of a particular target vessel. If the devices are designed for movement of a clot to the carotid artery, the size of the carotid artery can be used to select the device size without reference to the size of the vessel where the clot is initially located. In some embodiments relating to the use of a plurality of fibers to expand within the lumen of a patient's vessel, it is generally appropriate to use fibers that have a length from about 2.2 to about 15 times the vessel radius, in some embodiments from about 2.4 to about 12 times the vessel radius and in further embodiments from about 2.6 to about 8 times the vessel radius. As described above, the filter cartridge can further comprise metal elements radially below the polymer fibers that deploy to a reduced radial diameter. Based on the construction of the cartridge with the metal elements below the fibers and the fibers forming a matrix upon deployment, in the deployed configuration the metal elements form a scaffold under the polymer matrix with the polymer matrix protecting the vessel wall. The metal scaffold can essentially be up immediately below the polymer fibers pushed against the vessel wall. Generally, the unconstrained metal elements extend radially outward no more than about 94% of the outer extent of the polymer fibers, in further embodiments no more than about 90% and in additional embodiments no more than about 85% of the outer extent of the polymer fibers referenced from the central axis of the device. In some embodiments, if the fiber-based filter element is used to drag the clot into the carotid artery, the vessel diameter around the filter element can change, for example, from roughly 1.5 to 2 mm in diameter to about 5.5 to 6 mm in diameter. For placement in a human vessel, the fibers generally have a length from about 0.5 mm to about 60 mm, in other embodiments from about 1 mm to about 25 mm, and in further embodiments from about 2 mm to about 15 mm. A person of ordinary skill in the art will recognize that additional ranges of fiber numbers, fiber length and relative metal element extension within the explicit ranges are contemplated and are within the present disclosure.

In self actuating embodiments, the metal elements can be formed from shape memory metal, which for deployment is confined in the low profile configuration. Upon release of the constraints on the filter cartridge, the shape memory metal can resume an extended natural configuration designed in the element during its formation. For non-self extending structures, the metal elements may be formed to fold in a particular way when the ends are drawn to each other. For metal elements in a filter cartridge, the metal elements generally can have any reasonable cross sectional shape consistent with the element design, such as round, oval, ribbon shaped, or other reasonable cross sectional shape, and a circumference from about 0.0005 inches (12 microns) to about 0.025 inches (600 microns), in further embodiments from about 0.001 inches (24 microns) to about 0.02 inches (480 microns) and in other embodiments from about 0.002 inches (48 microns) to about 0.01 inches (240 microns). In general, a filter cartridge can comprise from about 2 to about 50 metal element, which can be designed to deploy at a reduced radial dimension as well as some metal elements placed to deploy with the polymer fibers to a larger radial dimension. A person of ordinary skill in the art will recognize that additional ranges of circumferences and number of metal elements within the explicit ranges above are contemplated and are within the present disclosure.

While generally the filter devices described in this section can be used in any appropriate medical procedure, especially in a patient's vasculature, these devices can be especially effective for use in systems designed for removing thrombus from cerebral vessel. In particular, the devices can be effective in combination with an aspiration catheter, and additional abrasive devices can be useful for disrupting a clot. The use of these devices for treatment of acute stroke events are described further below.

Stent Retrievers with Radially Flexible Frame and Polymer Cover

Stent retrievers with a slit along a generally cylindrical frame provide for radial flexible frame that can be combined with a polymer cover to cushion forces against the vessel wall. The frame generally is attached to a tether that extends from the treatment site external to the patient to provide for translational movement of the tent retriever to provide desired abrasive movement. The frame generally comprises a shape memory metal or the like so that the frame can extend up to the vessel wall without excessive forces due to the slit. Movement of the stent retriever can dislodge thrombus for removal from the vessel. In some embodiments, the distal end of the stent retriever can have a filtration structure, such as a porous sock-like extension or an extension of the cover material configured to fold into a closed tip, such that the stent retriever can also function as an embolic protection device.

Figure 16:
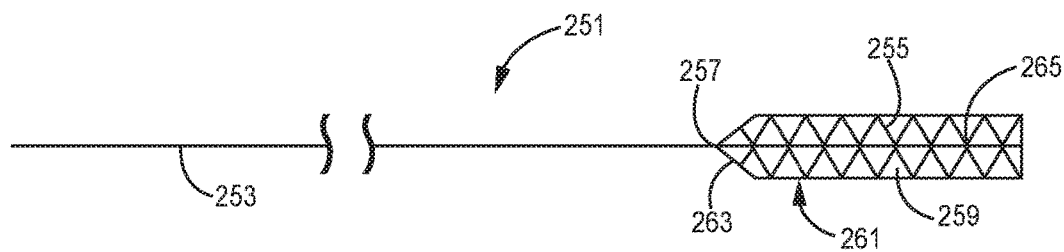
FIG. 16 is a side view of a stent retriever connected to a tether, the stent retriever having a cover and a slit.
Figure 17:
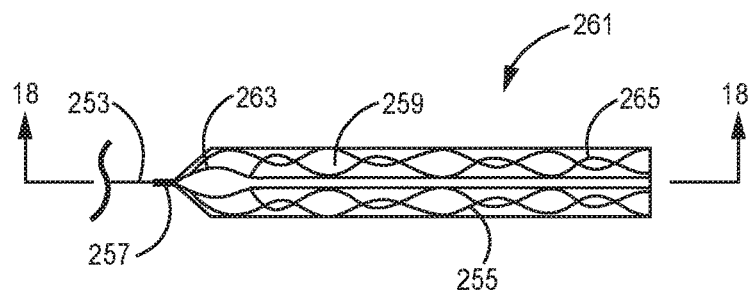
FIG. 17 is an expanded side fragmentary view of the stent retriever of FIG. 16.

Referring to FIGS. 16 and 17, a stent retriever 251 is shown comprising a tether 253, a metal frame 255, connector 257 and polymer cover 259. In additional or alternative embodiments, the stent retriever can also comprise a polymer liner that combines with the polymer cover to form a polymer sheet embedding the polymer frame. Tether 253 can be a wire, coil or the like. Tether 253 generally can have a length from about 30 cm to about 300 cm, in further embodiments from about 40 cm to about 250 cm, and the length may be selected depending on the specific procedure and vessel through which the device is introduced. Tether can have a diameter from about 0.001 inches to about 0.014 inches, in further embodiment from about 0.002 inches to about 0.01 inches and in additional embodiments from about 0.003 inches to about 0.008 inches. A person of ordinary skill in the art will recognize that additional ranges of tether dimensions within the explicit ranges above are contemplated and are within the present disclosure.

Figure 18:
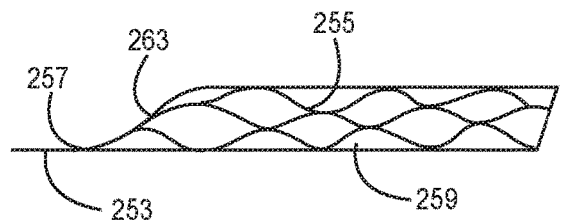
FIG. 18 is a section view of the stent retriever of FIG. 17 taken along line 18-18 of FIG. 17.

Metal frame 255 generally is self-extending, and can be formed from suitable metals, especially spring metals, such as nitinol or other shape memory alloys. Metal frame 255 can have articulating metal elements welded together to form a stable structure. The body of the frame can take any suitable stent structure that can transition from a low profile delivery configuration to an extended configuration. Additional description of stent retriever frames is presented in the following section. The body 261 of metal frame 255 generally is cylindrical if it is unconstrained, and the cylinder can have a proximal transition region 263 that open ups toward the connector 257, which, as attached at a point along the cylinder edge, as shown in the sectional view of FIG. 18. Metal frame 255 generally is out along a slit 265. Slit 265 can be straight along a line parallel to an axis of the cylinder, or slit 265 can have different shapes, such as a wave, that can function similarly. Connector 257 can be a weld of metal frame elements to the tether 253 and/or can comprise a mechanical fastener, such as a metal band which can be radiopaque.

Figure 19:
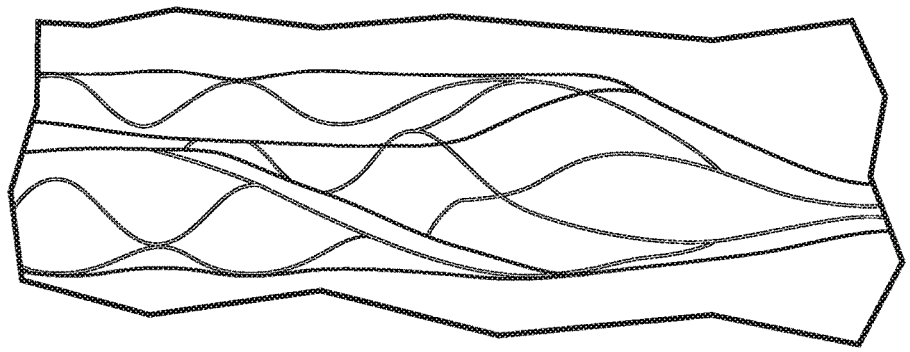
FIG. 19 is a photograph of a prototype of a stent retriever having a polymer cover and a slit.

Polymer cover 259 can be applied over the metal frame to provide a cushion for the metal frame against the vessel wall. Due to the extension of the device at deployment, the cover should appropriately adapt to the shape change. For example, a BioWeb™ Coating from Zeus®, which is an electro-spun PTFE web, see also U.S. Pat. No. 8,262,979 to Anneaux et al., entitled "Process of Making a Prosthetic Device From Electrospun Fibers," incorporated herein by reference. This material generally forms a liner such that the metal frame is laminated within polymer. A covered prototype with a BioWeb™ cover is shown in FIG. 19. Generally, a polymer liner may or may not also be used and can be formed from similar material. Similarly, a thin sheet of expanded polytetrafluoroethylene, (ePTFE) can be placed on the outside (and/or inside) of the metal frame with an adhesive or other suitable adhering approach, such as heat bonding and/or lamination. The use of ePTFE coatings for medical devices are described further in U.S. Pat. No. 8,641,777 to Strauss et al., entitled "Embolic Implant and Method of Use," incorporated herein by reference. A cover along with an optional liner can have a thickness from about 2 microns to about 100 microns and in further embodiments from about 4 microns to about 50 microns. A person of ordinary skill in the art will recognize that additional ranges of thicknesses within the explicit ranges above are contemplated and are within the present disclosure.

In some embodiments, a BioWeb™ cover or other cover material may form with openings through the web, and/or a cover can be processed to form holes through the coating, for example, using laser drilling. The holes drilled through the coating can facilitate flow through the coating. To the extent that the coating is intended to provide some degree of embolic protection, for example in which a cover can be designed to capture particles greater than 50 microns in diameter while allowing blood cells and beneficial blood components to continue to flow, the pores can be designed to provide appropriate flow through the cover. If the material is hydrophobic, larger pore sizes may be desirable to allow blood cells and other desirable blood components to flow through the pores, which can still be consistent with capture of desirable emboli.

In general, the cover can be attached to the metal frame in either an extended configuration or a low profile configuration. With a self extending frame, the process of securing the cover is more straightforward when the metal frame is in an extended configuration. For delivery, the improved stent retriever generally is placed into a reduced radially extending configuration, such as within the interior of a microcatheter. A covered stent retriever with a slit can be pulled into a microcatheter with forces applied when engaging the proximal transition region of the stent retriever against the opening of the microcatheter, the cylindrical section of the body can curl together due to the slit to achieve the reduction in radial extent.

When the stent retriever with a cover and slit is deployed in a blood vessel, the vessel walls generally constrain the expansion of the stent relative to its full unconstrained size.

Figure 20:
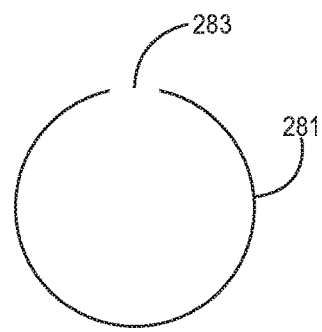
FIG. 20 is a sectional view of a cylindrical section of a constrained stent retriever with a slit.
Figure 21:
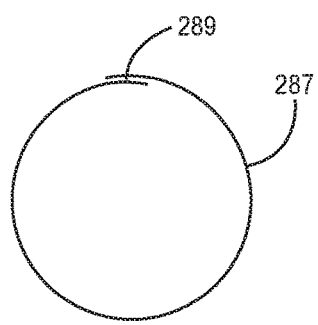
FIG. 21 is a sectional view of a cylindrical section of an alternative embodiment of a constrained stent retriever with a slit that has overlapping curled segments at the slit.

While blood vessels generally can have a more complicated architecture especially when thrombus is present, the basic structure is cylindrical and the constraining forces of the vessel wall generally reflect this structure. The stent structure generally can accommodate the constraining forces of the vessel wall either by limiting its radial extension and/or by rolling at the slit to decrease the expanded diameter. If both accommodations take place, the amount of overlap by rolling does not account fully for the decrease in device diameter relative to its unconstrained extension. These two circumstances are depicted separately in FIGS. 20 and 21. As shown in FIG. 20, stent retriever 281 expands to a certain diameter with a gap 283 due to the slit. As shown in FIG. 21, stent retriever 287 has an overlapping section 289 at the slit due to constraints not shown by a vessel wall.

For procedures in the cerebral arteries, the stent retriever described in this section can have lateral lengths from about 0.5 mm to about 2 centimeters and in further embodiments from about 1 mm to about 1 centimeter. The extended diameters can generally range from about 0.25 mm to about 3 mm, and in further embodiments from about 0.5 mm to about 2 mm. The stent retrievers can be provided in a set of sizes in which the medical professional can select an appropriate size. A person of ordinary skill in the art will recognize that additional ranges of sizes within the explicit ranges above are contemplated and are within the present disclosure.

The improved stent retriever with a cover and a slit can be used in various procedures described within the present application. For example, the stent retriever can be used with a filter devices such as the devices described in the previous section or similar devices A guide structure associated with a filter can pass through the interior of the cylinder of the stent retriever and the guide structure and tether can pass along side either other within a microcatheter or other catheter structures.

Figure 22:
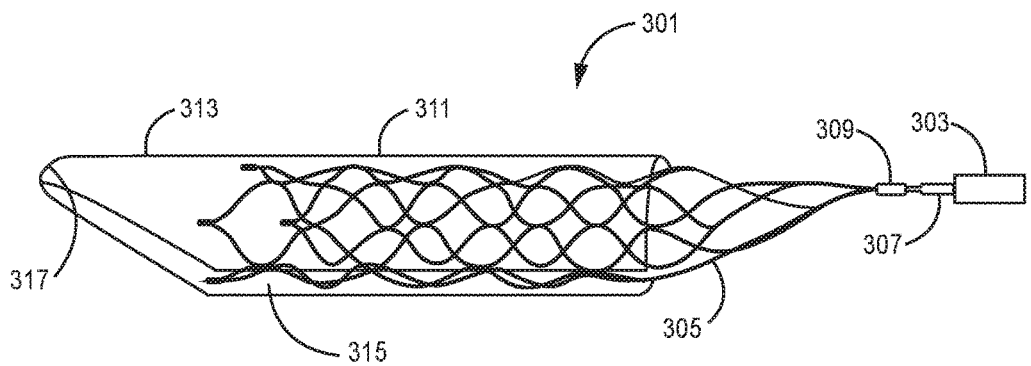
FIG. 22 is a fragmentary side view of a stent retriever embodiment with a distal extension of the cover to form a collector for loose clot fragments.

The distal end of the stent retriever can also be partially or fully closed off with porous polymer to provide embolic protection with the stent retriever itself. Referring to FIG. 22, Stent retriever 301 is shown extending from a microcatheter 303. With respect to stent retriever 301, metal frame 305 extends from tether 307 at connector 309. Polymer cover 311 covers the cylindrical section of metal frame 305 and has an extension 313 protruding in a distal direction from the end of metal frame 305. Slit 315 extends along the length of metal frame 305 and corresponding sections of polymer cover 311 as well as extension 313 up to a terminal enclosed pocket 317. When stent retriever 301 deploys with overlapping sections as shown in FIG. 21, extension 313 can fold over itself as an envelope to form a porous enclosure for the capture of emboli.

Figure 23:
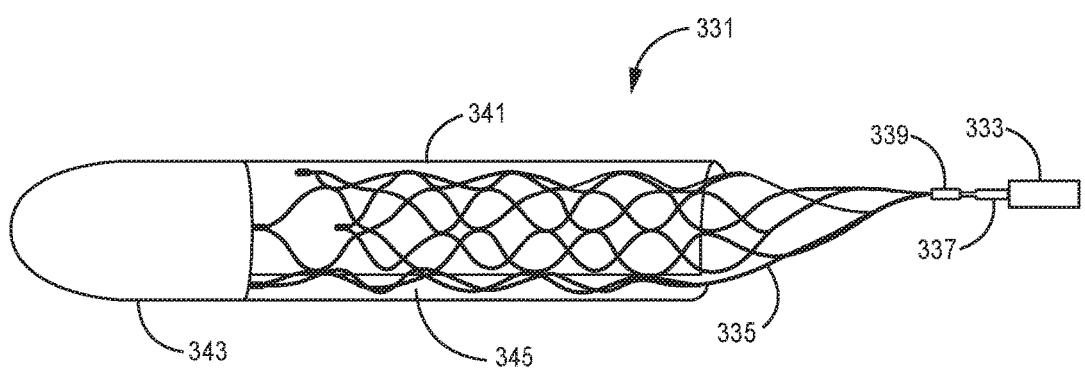
FIG. 23 is a fragmentary side view of a stent retriever embodiment with a distal pocket designed to provide embolic protection.

A further embodiment of a stent retriever with an embolic protection section at the distal end is shown in FIG. 23. Stent retriever 331 is shown extending from microcatheter 333. With respect to stent retriever 331, metal frame 335 extends from tether 337 at connector 339. Polymer cover 341 covers the cylindrical portions of metal frame 335. A pocket 343 of porous material extends in a distal direction from the end of metal frame 335. The exact shape of pocket 343 generally is considered not significant, but pocket 343 generally can capture emboli, such as clot fragments, while allowing the maintenance of reasonable flow downstream from stent retriever 331. In this embodiment, slit 345 only extends through the cylindrical portion of metal frame 335 and polymer cover 341. Pocket 343 can be formed of the material of polymer cover 341 or of a separate material, such as a PET polyester. A porous polyester material can be bonded to the metal frame with adhesive, heat bonding, mechanical fastening or combination thereof. The distal extensions in FIGS. 22 and 23 can generally be from about 1 mm to about 2 centimeters and in further embodiments from about 2 mm to about 1 centimeter. A person of ordinary skill in the art will recognize that additional ranges of distal length within the explicit ranges above are contemplated and are within the present disclosure.

Thrombectomy Devices Deploying Stents with Thrombus Abraders

Efficient procedures for the relief of an acute ischemic stroke condition can involve the use of devices mounted onto a microcatheter such that a reduced set of procedural steps can be involved. In some embodiments, it can be desirable to reduce the risk of damage to vessel walls such as through the application of abrasion within the lumen of a deployed stent. A sheath can be located over the microcatheter to control the release of devices delivered over the microcatheter. Various combinations of devices providing for stent delivery and for delivery of a mechanical abrader are described. In some embodiments, the devices can be delivered over a guide structure that supports a filter device, such as the filter devices described in the section above.

In the context of the present discussion, stents generally have an approximately cylindrical shape in an un-deployed configuration or an unconstrained deployed configuration as well as a structure having open walls through repositionable frame elements, although flexible coatings can be deployed over the frame structure. Stents have been used effectively to support the opening of blood vessels at occlusions. For example, stents have been used in coronary arteries, carotid arteries, saphenous vein grafts, other blood vessels as well as other bodily vessels, such as bile ducts, vessels of the urinary track, vessels of the reproductive track and the like. A stent generally can be delivered in a narrow profile, and the stent can be deployed into an extended configuration. Stents may be, for example, balloon extendable, self-extendable or extendable using any other reasonable mechanism. Self-extending stents can be constrained for delivery with a sheath or the like and deployed through release of the stent from the sheath. Self-extending stents can be desirable for the present applications due to a potentially lower radial profile in the delivery configuration, although stents with mechanical extension, such as balloon extension, can also be used. The stent upon deployment generally increases significantly in diameter. For example, the stent can be formed from a suitable material that is elastic and/or has a shape memory such that the stent material can expand as designed without breaking or excessively weakening. For example, stents can be formed from biocompatible metals, such as titanium, stainless steel, appropriate polymers and the like. Self-extending stents can be formed from shape memory materials, as described further below. At least a portion of the stent can be made radiopaque to provide for guiding procedures to obtain desired protection from the stent, and in some embodiments, effectively the entire stent is formed from a radiopaque material.

Self-expanding stents are described further in U.S. Pat. No. 8,764,813 to Jantzen et al., entitled "Gradually Self-Expanding Stent" and U.S. Pat. No. 8,419,786 to Cottone, Jr. et al., entitled "Self-Expanding Stent," both of which are incorporated herein by reference. Balloon extendable stents can be crimped to the balloon for delivery. Some balloon-stent structures are described further, for example, in U.S. Pat. No. 6,106,530 to Harada, entitled "Stent Delivery Device;" U.S. Pat. No. 6,364,894 to Healy et al., entitled "Method of Making an Angioplasty Balloon Catheter;" and U.S. Pat. No. 6,156,005 to Theron, entitled "Ballon [sic] Catheter for Stent Implantation," each of which are incorporated herein by reference.

Stents and balloons associated with therapeutic agents are described further in U.S. Pat. No. 6,491,617 to Ogle et al., entitled "Medical Devices That Resist Restenosis," incorporated herein by reference. Drug coated stents have been sold commercially. Examples of commercial coronary stents include, Cypher™ from Cordis/Johnson & Johnson, which has a coating that elutes sirolimus from a PEVA and PBMA, Taxus™ from Boston Scientific, which has a coating that elutes paclitaxel from SIBS copolymer coating and Endeavor™ from Medtronic which has a coating that elutes zotarolimus from phophorylcholine. These particular coated stents are for coronary use. Drug coated stents can be appropriate for the present methods to inhibit restenosis, and the specific examples above would be suitable but not limited to this list.

Figure 24:
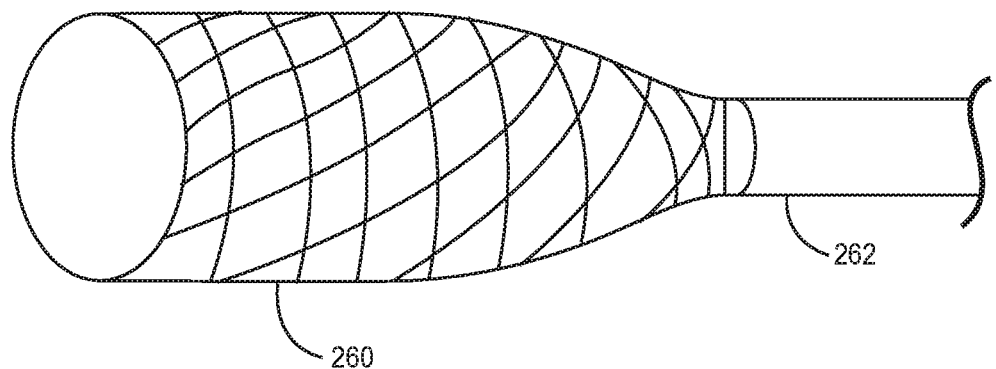
FIG. 24 is a prospective side view of a self-expanding stent released from a microcatheter sheath.
Figure 25:
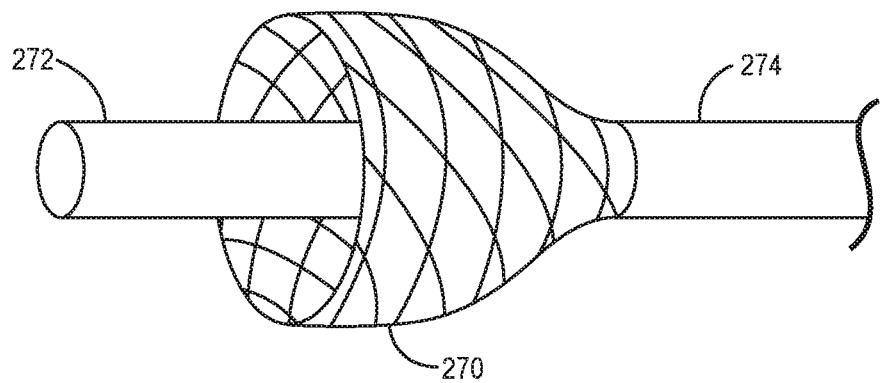
FIG. 25 is a prospective side view of a self-expanding stent being released from the surface of a microcatheter by sliding back a restraining sheath.

For the procedures described herein, stents can be used to stabilize the vessel at points of occlusion while thrombus can be removed using protection of the vessel provided by the stent. During the procedure as some thrombus is removed, a self-extending stent may continue to further extend as the procedure progresses. A schematic depiction of a self-expanding stent 260 released from a microcatheter sheath 262 is shown in FIG. 24. A schematic depiction of a self-expanding stent 270 being released from the exterior of a microcatheter 272 by sliding back a separate sheath 274 is shown in FIG. 25. The approaches in FIGS. 24 and 25 depict alternatives for the delivery of a stent based on a microcatheter.

Abrading apparatuses, or atherectomy devices, can be used to dislodge thrombus within arteries of the brain such that the clots or fragments thereof can be more readily removed. Atherectomy devices are described, for example, in U.S. Pat. No. 5,100,425 to Fischell et al., entitled "Expandable Transluminal Atherectomy Catheter System and Method for the Treatment of Arterial Stenoses," incorporated herein by reference. In general, the use of an atherectomy device in the blood vessels of the brain is concerning with respect to damage to the vessel wall that can result in a hemorrhagic stroke. In the methods described herein, the atherectomy procedure is performed within the lumen of the stent that provides protection to the vessel wall. The use of an extendable atherectomy tool can provide for delivery into the vessel to the interior of the stent. Radiopaque markers on the stent and the atherectomy device can provide for alignment of the atherectomy cutting element within the stent.

Figure 26:
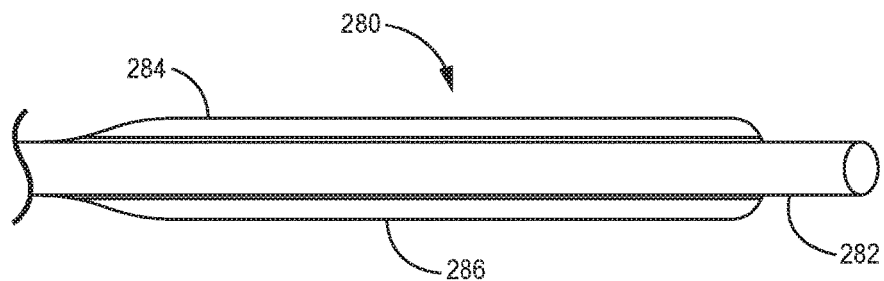
FIG. 26 is a fragmentary perspective side view of an atherectomy device in an unextended configuration with a shaft supporting two cutting blades.
Figure 27:
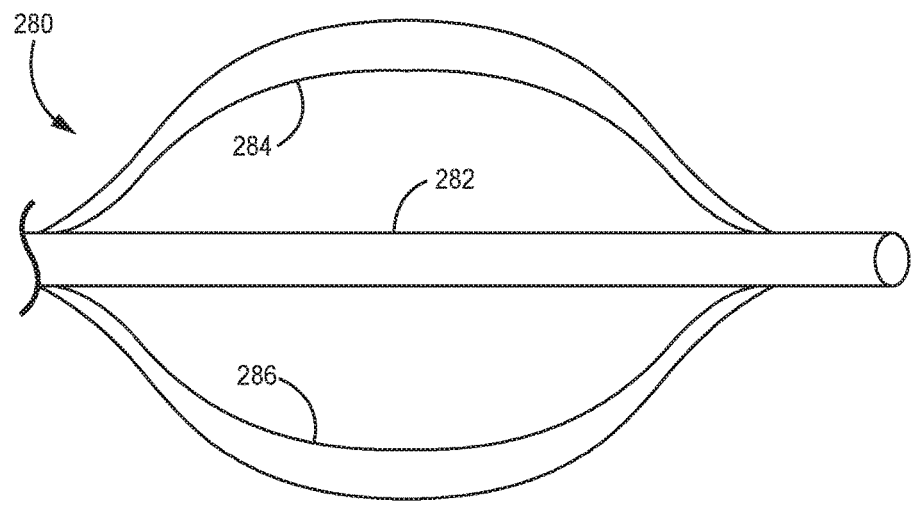
FIG. 27 is a fragmentary perspective side view of the atherectomy device of FIG. 24 in an extended configuration.

In some embodiments, the atherectomy cutting tool can have flexible cutting elements that can be rotated, in which the rotation or other actuation components applies forces that flare out and extend the cutting elements to engage thrombus. A schematic depiction of a suitable embodiment of a rotation powered atherectomy device is depicted in FIG. 26 (un-deployed) and 27 (deployed). Atherectomy device 280 comprises a shaft 282 and two extendable cutting elements 284, 286. In the un-deployed configuration of FIG. 26, cutting elements 284, 286 lay adjacent shaft 282 in a low profile configuration. Shaft 282 can be configured to rotate. Either the forces of the rotational motion or some actuation mechanism can transition cutting elements 284, 286 into an extended configuration as shown in FIG. 27. Cutting elements can be polymer material that extends with the application of rotational force, or a metal structure with pivots or an unfolding configuration that extends upon application of rotation. While generally a range of abrasive elements can in principle be used such as a device as in FIGS. 26 and 27, manual devices using mostly or exclusively translational motion can be desirable from a balance of factors including, for example, a more flexible construction for delivery into tortuous vessels and lower risk of damage to vessel walls. Thus, the remaining discussion focuses on a stent retriever style atherectomy devices.

Stent retrievers are term given to abrasive devices that have components reminiscent of a vascular stent that are attached to a tether so that they can be dragged in a blood vessel to loosen or entrap clots for removal from the vessel. Generally, stent retrievers comprise an open metal frame, which can be grid with woven or joined crossing metal features, although the components can comprise coils or the like. Several versions of stent retrievers are commercially available, such as Solitaire™ (Covidien/Medtronic), Trevo® (Stryker) and Merci™ (Concentric Medical). An expandable device for thrombus removal is described in U.S. Pat. No. 8,945,143B2 to Ferrera et al. (Covidien), entitled "Expandable Tip Assembly for Thrombus Management," incorporated herein by reference. Another stent retriever device is described in published U.S. patent application 2012/0123466A1 to Porter et al, (Stryker) entitled "Axially Variable Radial Pressure Cages for Clot Capture," incorporated herein by reference. Vascular stents as well as stent retrievers generally comprise metal wires that can be formed into a pattern for engagement with a vessel wall. Stent retrievers may or may not form a generally cylindrical section. For use in the vessel protective systems described herein, in some embodiments, it can be desirable to have the abrasive device mounted on a microcatheter to facilitate the procedures described herein.

If a stent retriever is made of a shape memory material, a self-extending stent retriever may be released from a sheath to extend outward from the outer surface of the microcatheter or from an anchor to a guide structure. For appropriate embodiments, once the microcatheter is at the treatment site, a sheath over the microcatheter surface can be translated in a proximal direction relative to the microcatheter, releasing the stent retriever. The stent retriever can be attached at or near one end, at or near both ends, or at other convenient points to keep the stent retriever connected to the microcatheter or other structure.

Specifically, devices incorporating aspects of a stent retriever combined with a microcatheter can provide effective designs for performing the atherectomy procedures described herein. Microcatheters have been designed to allow for access to cerebral blood vessels. As such, the microcatheter can facilitate various aspects of the procedure. In embodiments involving the removal of the microcatheter to provide for the delivery of an atherectomy element, additional steps of the procedure may be implicated, and such a procedure detracts from the possible functional contributions from the microcatheter without the replacement of the microcatheter at a later stage of the procedure. Thus, the availability of an atherectomy element associated with the microcatheter can provide desired functionality in an effective format suitable for efficient procedures. At least a portion of the atherectomy element, such as a stent retriever, can have a radiopaque material, such as a marker band, radiopaque components or the like, to direct use of the device under x-ray visualization.

Microcatheters can be adapted for use in small blood vessels, for example in the brain. Of course, the term microcatheter can cover a range of devices, and the present discussion can focus on catheters useful for the procedures described herein. In some embodiments, microcatheters can comprise a distal section that is narrower than a proximal section. However, in further embodiments, a microcatheter can have an approximately constant diameter along its length to facilitate delivery of other devices over the microcatheter. A narrow distal diameter allows for the catheter to navigate the tortuous vessels of the brain. The distal section can be sufficiently flexible to allow navigation of the vessels, but resilient enough to resist kinking. A mierocatheter comprises at least one lumen. The microcatheter can then be used to deliver other treatment devices, aspiration, fluid profusion, therapeutic agents, or other means of treating a condition. While microcatheters can have a selected size, in some embodiments, the microcatheters can have a distal outer diameter from about 1.0 Fr to about 3.5 Fr and a length from about 75 cm to about 300 cm and in further embodiments from about 1.2 Fr to about 3 Fr and a length from about 100 cm to about 200 em. A person of ordinary skill in the art will recognize that additional size ranges within the explicit ranges above are contemplated and are within the present disclosure.

It can be desirable for the stents and/or the stent retrievers described herein to be self extending. The self-extending feature can be introduced using shape memory materials, such as spring metals or the like. Suitable spring metals that can be used for self actuating struts include, for example, cobalt alloys, such as Elgiloy®, a cobalt-chromium-nickel alloy, MP35N, a nickel-cobalt-chromium-molybdenum alloy, and nitinol, a nickel-titanium alloy. In other embodiments, other metals can be used, such as stainless steel, titanium or other medical metals. Furthermore, the devices can comprise radiopaque structures, components or the like to enhance visualization by x-ray during the procedure. Alternatively or additionally, the structures can comprise polymers, such as polyethylene terephthalate, polyimide, polycarbonate, polyether ether ketone (PEEK), combinations thereof or the like.

Figure 28:
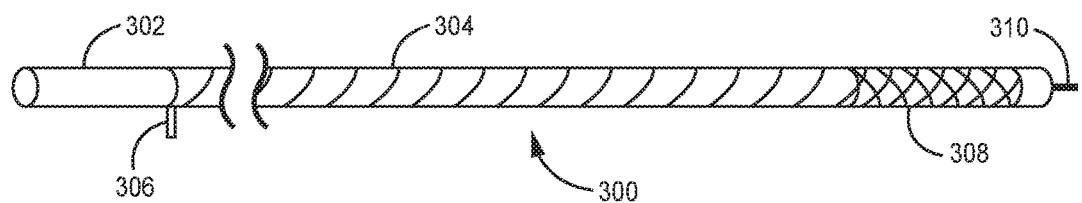
FIG. 28 is a perspective side view of a microcatheter with a treatment device in a delivery configuration under a sheath.

Some specific embodiments for stents and stent retrievers for delivery with a microcatheter are described in FIGS. 28-37. Referring to FIG. 28, a suitable configuration of a treatment device 300 is depicted with a configuration for the delivery of both a stent and a stent retriever with a microcatheter. Treatment device 300 comprises microcatheter 302, sheath 304 with a handle 306 to facilitate sliding of the sheath over the microcatheter, a first self-extending treatment element 308 (e.g., a stent or abrasive element), and a second treatment element 310 within the lumen of the microcatheter, which may be self extending or not and generally is the complimentary element to first treatment element 308, such as a stent if the first treatment element is a stent retriever or such as a stent retriever if the first treatment element is a stent. While handle 306 is depicted with one particular design, any reasonable design can be used, such as a knob around the circumference of sheath 304 or other designs that can be conveniently used by the user. Handle 306 and corresponding portions of the microcatheter are intended to remain outside of the patient through the procedure.

Two optional versions of the treatment device can be based on this basic design. In a first version, a stent retriever is loaded on the outer surface of the microcatheter, and a stent is loaded within the microcatheter. In the second version, a stent is loaded on the outer surface of the microcatheter, and a stent retriever is loaded within the microcatheter. In either version, the component delivered on the outer surface of the microcatheter, either the stent retriever or the stent, can be covered with the sheath that restrains the component until positioned for release. The sheath can be moved in a proximal direction relative to the microcatheter to release the initially covered component for deployment, generally through self-extension. Both versions can be suitable for delivery over a guide structure passing within the microcatheter. Of course, the two versions of the device generally involve correspondingly modified procedure for delivery of the devices, as noted further below.

Figure 29:
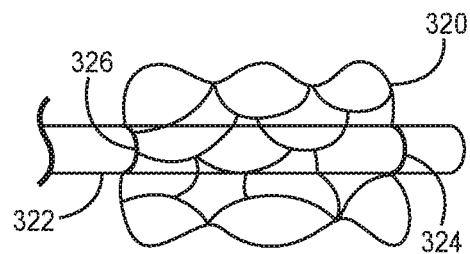
FIG. 29 is a fragmentary side view of a stent retriever secured to a microcatheter at a distal and proximal locations.
Figure 30:
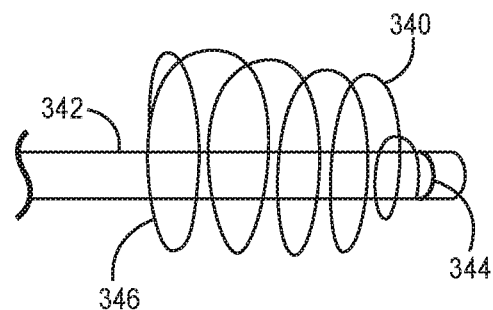
FIG. 30 is a fragmentary side view of a stent retriever connected to a microcatheter at a distal location.
Figure 31:
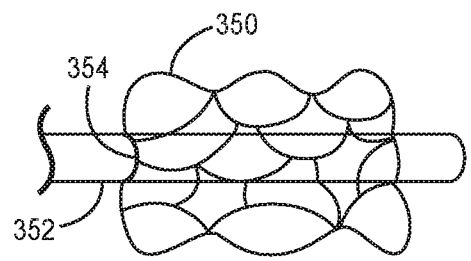
FIG. 31 is a fragmentary side view of a stent retriever connected to a microcatheter at a proximal location.

As noted above, the delivery of a stent retriever mounted onto the surface of a microcatheter or the like provides a desirable device for a range of procedures. With the stent retriever mounted on the microcatheter, the device can be delivered over a guide structure, such as a guide structure supporting a fiber based filter element for embolic protection. Three embodiments are shown schematically in FIGS. 29-31, respectively. In FIG. 29, stent retriever 320 has attachments to the microcatheter 322 at or near the distal end 324 and at or near the proximal end 326 of stent retriever 320. In FIG. 30, stent retriever 340 is secured to microcatheter 342 only at or near the distal end 344 of stent retriever 340 with unsecured proximal end 346. Referring to FIG. 31, stent retriever 350 is secured to microcatheter 352 only at or near the proximal end 354 of stent retriever 350. In further embodiments, a stent retriever may be secured to a microcatheter away from the ends of the stent retriever at one or a plurality of locations as an alternative or an addition to being secured at or near the distal end and/or the proximal end.

Figure 32:
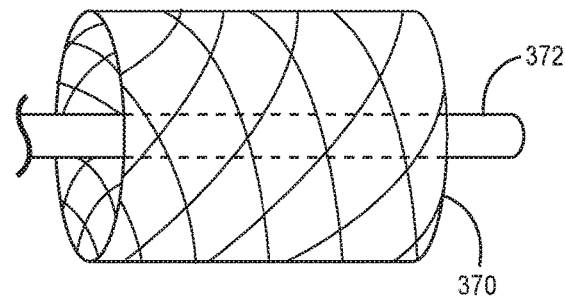
FIG. 32 is a fragmentary perspective side view of an extended stent with a microcatheter extending through the lumen of the extended stent.

Referring to FIG. 32, in contrast to the embodiments in FIGS. 29-31, when a self-expanding stent 370 is released at the surface of a microcatheter 372, extended stent 370 is not constrained through attachment to microcatheter 372. While versions of the devices in FIGS. 29-32 can be effectively used in the procedures described herein without being part of devices comprising both a stent and stent retriever in a single device, embodiments having both a stent and stent retriever delivered with single device can provide for performance of a convenient delivery procedure. Generally, for use in the procedures described herein, it can be desirable for treatment devices to be useful with a embolic protection device supported with a guide structure, such as those described above, to be in position and deployed during the period in which the stent and stent retriever are manipulated to capture any traveling emboli generated during the manipulation of the stent and/or stent retriever.

Figure 33:
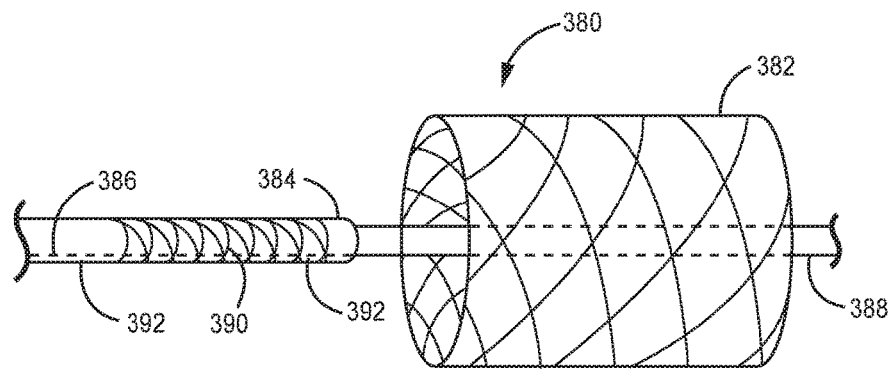
FIG. 33 is a side view of an extended stent with a guide structure extending through the lumen of the stent and a microcatheter over the guide structure proximal to the stent with a stent retriever positioned on the outer surface of the microcatheter covered with a sheath.

Referring to FIG. 33, an embodiment of a treatment device 380 is shown in which a stent 382 has been deployed from the interior of a microcatheter 384. The delivery of stent 382 can be effected through the siding of a delivery device, such as a push catheter, within the interior of microcatheter 384. In particular, a delivery device 386 can be a push wire or a sheath-like structure that slides along the interior surface of microcatheter 384 that can be moved in a distal direction to push stent 382 from the interior of microcatheter 384. Once stent 382 has exited the interior of microcatheter 384, stent 382 can be in its extended state through self actuation or action of an actuation element, such as a balloon or the like. With the constraints of the vessel present, generally the extended stent presses against the vessel wall. As shown in FIG. 33, microcatheter 384 can be initially in a proximal direction relative to extended stent 382 following the deployment of the stent, and microcatheter 384 can be moved in a distal direction, such as past the sent, over a guide structure 388, if present, to position a stent retriever 390 within stent 382 or distal to stent 382 when stent retriever 390 is released from constraint by sheath 392 along the surface of microcatheter 384 to take its extended shape. Extended stent retriever 390 can be moved within 1$ the vessel through movement of microcatheter 384 to exhibit the abrading function of stent retriever 390.

Figure 34:
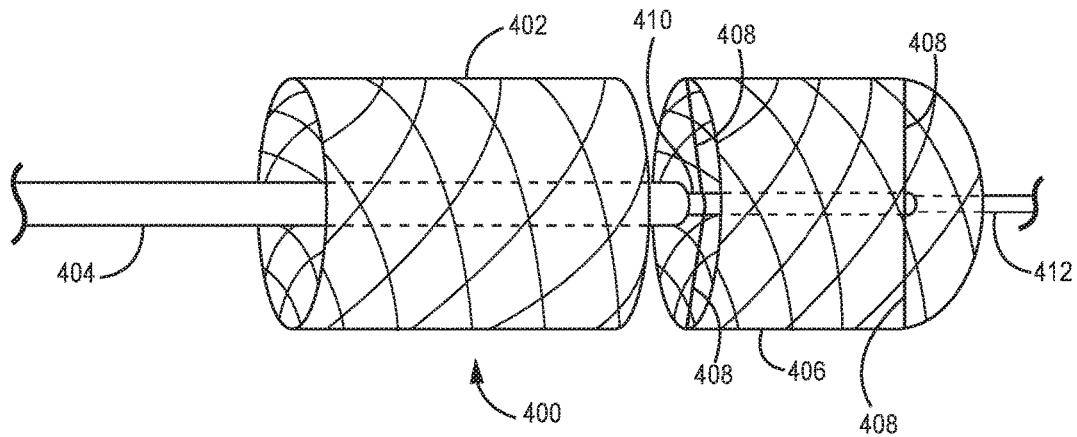
FIG. 34 is a side view of an extended stent with a microcatheter extending through the stent lumen, a stent retriever deployed distal to the microcatheter on a support and a guide structure extending distal to the stent retriever.

Referring to FIG. 34, an embodiment of a treatment device 400 is shown with a stent 402 mounted on the exterior of a microcatheter 404 and a stent retriever 406 is delivered from the interior of microcatheter 404. As shown in FIG. 34, both stent 402 and stent retriever 406 are in extended configurations. In the depicted embodiment, stent retriever 406 is secured with tethers 408 to a support structure 410, which can be a catheter or other pushable structure over guide structure 412. Since in this embodiment stent retriever 406 is naturally deployed distal to the microcatheter and the stent is deployed from a position over the microcatheter, the microcatheter is not necessarily moved to effectuate the appropriate delivery of both components. However, after delivery of the stent, it may be desirable to move microcatheter 404 some distance proximal to stent 402 prior to deployment of stent retriever 406 in view of the protection to the vessel wall provided by stent 402. Since neither deployed component is connected to the microcatheter, the microcatheter can be withdrawn in a proximal direction away from the treatment site to allow for the atherectomy procedure or other steps in the overall procedure.

In the procedures of particular interest described herein, the direct interaction of thrombus with a stent and/or stent retriever can be performed with an embolic protection device in a deployed configuration. Embolic protection devices of particular interest are supported on a guide structure that generally extends from outside of the patient past the occlusion/clot, and convenient embodiments are described above. In principle, a stent retriever can be attached to a control wire without direct interaction with the guide structure that can be configured to move independently of the stent retriever. However, in some embodiments, it can be desirable for the stent retriever to have specific structures to guide the movement of the stent retriever relative to the guide structure.

Figure 35:
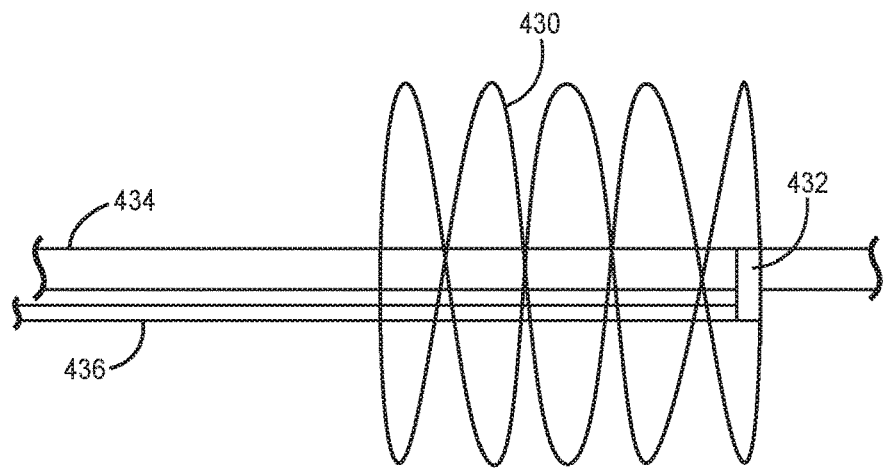
FIG. 35 is a fragmentary side view of a stent retriever mounted to a guide structure at a distal slide with a control wire.
Figure 36:
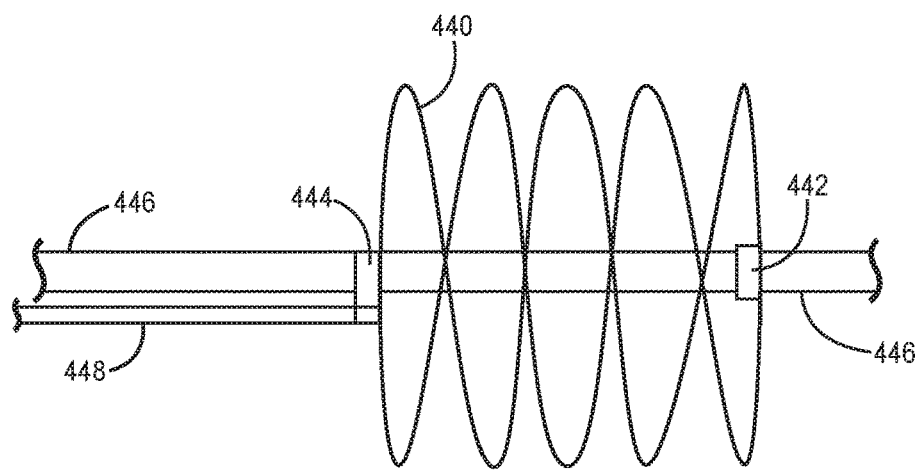
FIG. 36 is a fragmentary side view of a stent retriever mounted to a guide structure with a distal slide and proximal slide with the proximal slide connected to a control wire.
Figure 37:
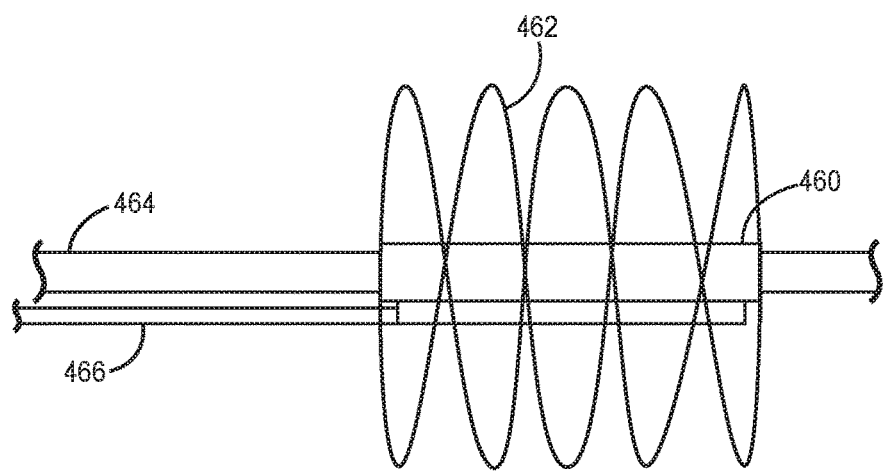
FIG. 37 is a fragmentary side view of a stent retriever connected to a guide structure with a tubular slide that is further attached to a control wire.

Referring to FIGS. 35-37, three alternative embodiments are depicted for stent retrievers suitable for deployment from the interior of a microcatheter with a guide structure passing through the interior of the microcatheter. Referring to FIG. 35, a stent retriever 430 is attached to a slide 432 that is configured to slide over guide structure 434. A control wire 436 is attached to slide 432 to facilitate the relative movement of stent retriever 430 relative to guide structure 434. Slide 432 is attached at or near the distal end of stent retriever 430, but a connection can be made at other locations along stent retriever 430. Also, stent retriever 430 can be attached to the control wire at other locations not associated with slide 432, alternatively or additionally attached to the slide.

Referring to FIG. 36, a stent retriever 440 is attached to a distal slide 442 and a proximal slide 444, in which distal slide 442 and proximal slide 444 are configured for sliding over a guide structure 446. Control wire 448 is shown connected to proximal slide 444, but control wire 448 can additionally or alternatively be connected to distal slide 442, both proximal slide 444 and distal slide 442 and/or positions of stent retriever 440 not associated with a slide. Referring to FIG. 37, a tubular slide 460 is shown that extends for roughly the entire length of stent retriever 462, although an alternative tubular slide can extend for about 25% to about 150% of the length of stent retriever 462 along guide structure 464. A control wire 466 can be attached to a selected portion of tubular slide 460 or attached along the entire length of slide 460.

For procedures in the cerebral arteries, stents and stent retrievers can have lateral lengths from about 0.5 mm to about 2 centimeters and in further embodiments from about 1 mm to about 1 centimeter. The extended diameters can generally range from about 0.25 min to about 3 mm, and in further embodiments from about 0.5 mm to about 2 mm. The stents and stent retrievers can be provided in a set of sizes in which the medical professional can select an appropriate size. A person of ordinary skill in the art will recognize that additional ranges of sizes within the explicit ranges above are contemplated and are within the present disclosure.

While the devices described in this section can be used for a range of procedures, as noted above, these devices can be especially desirable for procedures in cerebral arteries. Also, while these devices can be used alone, as noted above, it is generally desirable to use with a filter device downstream from the stent retriever to capture any released emboli. Also, it can be desirable to further use an aspiration catheter to remove clots or fragments thereof loosened during the procedure. Suitable procedures are described further in the following section.

Occlusion Treatment Systems and Methods

Various components for treatment of vascular occlusions can be used individually or in various groupings. Desirable groupings are described in the following along with methods of using the device and systems, especially for acute ischemic stroke, treatments. The procedures generally make use of an aspiration catheter that is positioned proximal to the occlusion such that aspiration can be applied during selected portions of the procedure, such as steps of the procedure that can generate emboli. A filter device can be placed distal to the occlusion and can catch at least some emboli if they flow down stream as well as possible contributing to the manual removal of thrombus. In some embodiments, the filter device and aspiration catheter can set boundaries on the treatment zone, and additional components may or may not be used, such as stents and/or stent retrievers, within the treatment zone. In some embodiments, liquid can be profused into the treatment zone, for example, out from a microcatheter, to make up for at least some fluid removed from the treatment zone by aspiration.

The basic systems for the procedures described in this section comprise a suction catheter and a filter device mounted on a guide structure. Other basic devices can include, for example, a guide wire, a guide catheter and a microcatheter. Use of these devices are described as a system for some examples of procedures. In a further set of example procedures, stents and stent retrievers from the previous section are added for the procedures.

An aspiration catheter can be an effective component for the removal of cerebral clots, even if used alone. When aspiration catheters are combined with the other elements described herein, the combined treatment systems can offer several elements in the cooperative efforts to remove the clot, although the aspiration catheter may be effective when used alone. The aspiration catheter provides removal forces from the proximal side of the treatment system while a filter device can provide the distal backstop, although a fiber based filter can in principle be extended in the clot to engage the clot for pulling.

Figure 38:
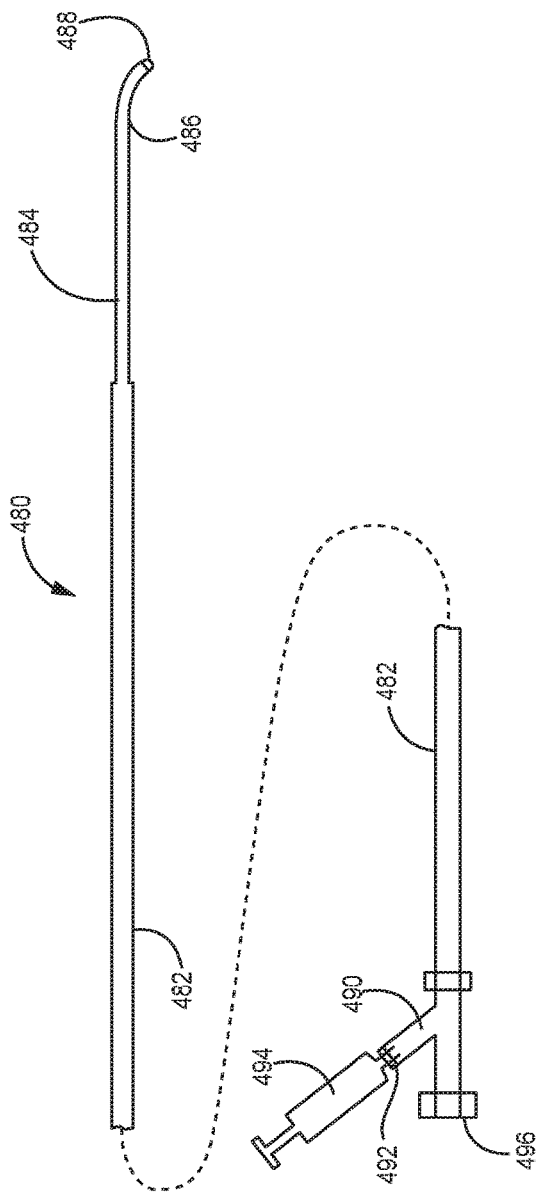
FIG. 38 is a side view of an aspiration catheter with a narrow diameter distal tip for accessing small vessels, such as the neurovasculature while providing strong suction.

Various aspiration catheters have been developed for providing improved suction within the narrow tortuous vessels of the cerebral vasculature. In some embodiments, these aspiration catheters have a narrowed distal tip that can reach into narrow vessels but provide high flows out of the vessel due to the larger proximal lumen. These improved designs are described in published U.S. patent application 2011/0230859 to Galdonik et al., entitled "Aspiration Catheters for Thrombus Removal," incorporated herein by reference. Referring to FIG. 38, aspiration catheter 480 for accessing smaller vessels comprises a tube 482, a reduced diameter distal segment 484 with an average diameter smaller relative to the average diameter of the tube, an optional curved distal tip 486, a radiopaque marker band 488, which may be at or near the distal tip whether or not curved, a proximal end 490, an aspiration connection 492, a suction device 494, and a proximal port 496 for insertion of guide structures or other devices through the catheter lumen. Aspiration catheter 480 can optionally have a rapid exchange configuration with a rapid exchange port. Aspiration connection 492 can comprise a fitting or the like to provide a sealed connection with the suction device 494, or suction device 494 can be formed as an integral part of the proximal end 490 such that aspiration connection 492 is the integral connection. Suitable suction devices include, a suction device that can deliver a selected amount of suction, such as a syringe, a compressed bladder, a pump, such as a peristaltic pump or a piston pump, or the like.

Distal segment 484 can have an outer diameter from about 25 percent to about 95 percent of the average outer diameter of tube 482 of the catheter, and in further embodiments from about 45 to about 90 percent and in additional embodiments from about 60 to about 85 percent of the average diameter of the tube. For example, distal segment 484 can have an outer diameter range from about 0.015 to about 0.120 inches, and tube 482 can have an outer diameter range from about 0.030 to about 0.150 inches, in other embodiments from about 0.040 to about 0.125 inches and in further embodiments from about 0.045 to about 0.120 inches. A person of ordinary skill in the art will recognize that additional ranges of dimensions within the explicit ranges above are contemplated and are within the present disclosure. In optional embodiments, a bent or curved tip can provide improved tracking during delivery into a patient's vessel by controlling tracking along a guide structure extending from the tip.

Aspiration catheters with a narrowed distal segment approved and commercially available for neurovascular procedures include MI-AXIS™ (MIVI Neuroscience, Inc.) and MAX™ catheters (Penumbra). A new design is based on the use of a guide catheter to function as a part of aspiration lumen with a narrowed extension of the aspiration catheter extending from the guide catheter. See copending U.S. patent application Ser. No. 14/949,574 to Ogle et al, entitled "Catheter Systems for Applying Effective Suction in Remote Vessels and Thrombectomy Procedures Facilitated by Catheter Systems," incorporated herein by reference. An embodiment of these nozzle type aspiration catheters is shown in FIGS. 39 and 40.

Figure 39:
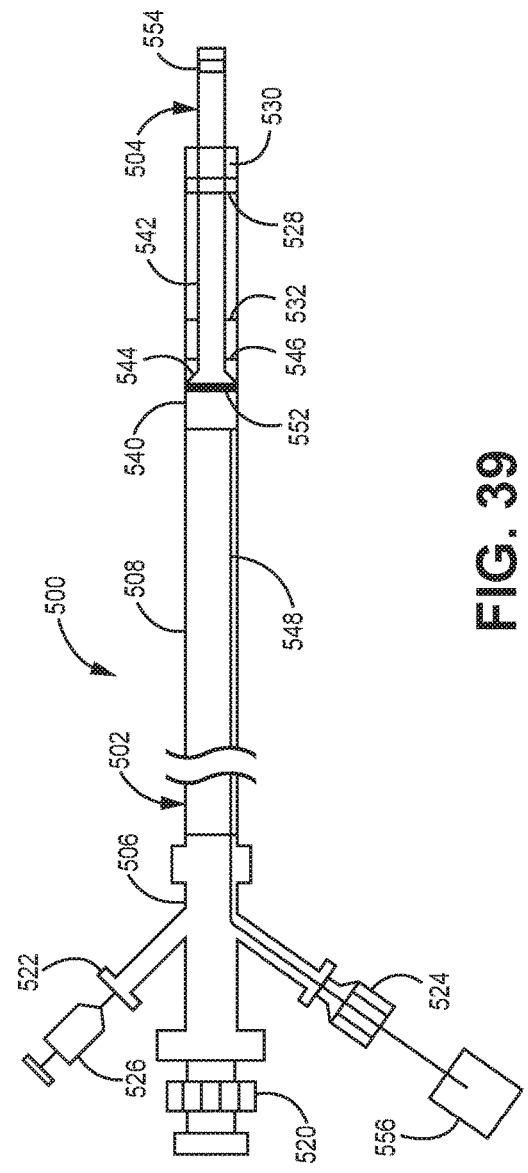
FIG. 39 is a side view of a suction system comprising a guide catheter with a suction extension with the guide catheter shown as transparent to allow visualization of structure within the guide catheter.
Figure 40:
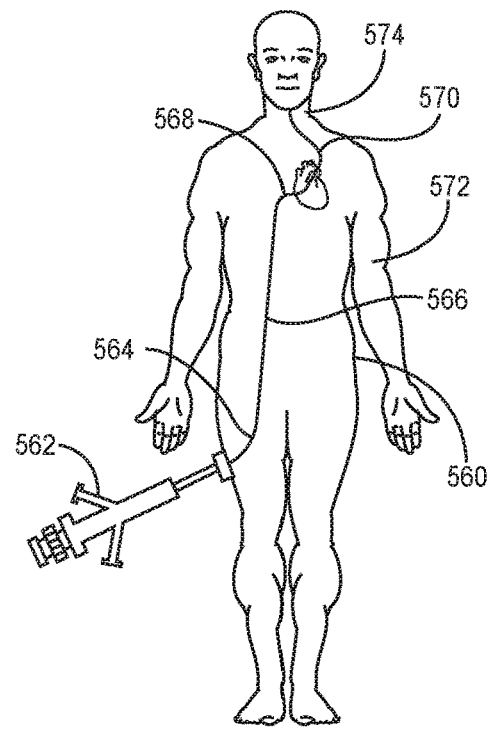
FIG. 40 is a schematic drawing of a human patient with a treatment system as described herein entering the patient at the femoral artery and extending into a cerebral artery.

Referring to FIG. 39, suction system 500 comprises a suction adapted guide catheter 502 and a suction extension 504. The suction adapted guide catheter 502 comprises proximal section 506 and tubular shaft 508. Proximal section 506 generally is suitable for use also as a handle and generally can comprise a proximal fitting 520, a suction port 522 and an optional control wire port 524, as well as possibly other additional ports and/or fittings to provide desired functionality and access, in which all such ports and fittings can be arranged in a branch configuration or other suitable configuration. Proximal fitting 520 can comprise a suitable hemostatic valve, Luer fitting or the like to provide for entry of a guidewire and/or structures delivered over the guidewire into the guide catheter lumen, such as alternative treatment structures and/or embolic protection devices. As shown in FIG. 39, a negative pressure device 526 is shown connected with suction port 522, and suitable negative pressure devices include, for example, syringes, pumps, such as peristaltic pumps, piston pumps or other suitable pumps, aspirator/venturi, or the like.

Tubular shaft 508 can have an approximately constant diameter along its length, or the guide catheter can have sections with different diameters, generally with a smaller diameter section distal to a larger diameter section. Tubular shaft 508 can have one or more radiopaque marker bands to facilitate positioning of the tubular shaft within the patient, and FIG. 39 shows a marker band 528 near the distal end of tubular shaft 508, although additional positions and/or alternative positions can be used as desired. At or near the distal end of the shaft, a stop 530 is positioned to retain a portion of suction extension 504 within the lumen of tubular shaft 508. Tubular shaft 508 can further comprise a seal 532 to provide for reducing or eliminating any flow within tubular shaft 508 that avoids suction extension 504. In some embodiments, seal 532 can be combined with stop 530, or seal 532 as a distinct element can be avoided through a design with a sufficiently tight fit between suction extension 504 and the lumen wall of tubular shaft 508.

Suction extension 504 can comprises a proximal portion 540, suction tip 542, connection portion 544, optional engagement element 546 and control structure 548, such as a control wire. All or a part of proximal portion 540 can be configured to remain within the lumen of guide catheter 502. As shown in FIG. 39, proximal portion 540 comprises a radiopaque marker band 552, although proximal portion may not have a marker band in some embodiments and in other embodiments can comprise a plurality of marker bands. Suction tip 542 is shown with radiopaque marker band 554 near the distal tip of suction tip 542, although again suction tip 542 can comprise a plurality of radiopaque marker bands if desired. Connection portion 544 connects proximal portion 540 and suction tip 542, which can be a transition portion that gradually changes diameter or a connector that forms a seal between the proximal portion and suction tip. Optional engagement element 546 can engage stop 530 to establish the distal placement limit of suction extension 504 relative to guide catheter 502. In some embodiments, stop 530 is configured to engage an edge or other limiting structure of proximal portion 540 so that engagement element 546 is effectively integrated with the proximal portion 540 or connection portion 542. Control structure 548 can be a control wire or the like that connects with proximal portion 540 and extends exterior to the catheter, such as exiting through control wire port 524. Control structure 548 can be used to control positioning of proximal portion 540 within the lumen of tubular shaft 508. Control structure 548 can comprise a control tool 556, such as a handle, slide or other the like that can anchor a control wire or other connecting element to facilitate movement of the control wire. In some embodiments, the clearance can be made sufficiently small between the outer surface of proximal portion 540 and the inner surface of tubular shaft 508 that a separate seal is not needed.

The guide catheter can have an outer diameter from about 5.5 Fr (1.667 mm diameter) to about 10 Fr (3.333 mm diameter), in further embodiments from about 6 Fr (1.833 mm diameter) to about 9 Fr (3 mm diameter), and in some embodiments from about 6.25 Fr (2 mm diameter) to about 8.5 Fr (2.833 mm diameter). The guide catheter measurement are generally referenced to the outer diameter, and the inner diameter is less than the outer diameter by twice the wall thickness. The length of the guide catheter can be from about 30 cm to about 150 cm, in further embodiments from about 35 cm to about 130 cm and in additional embodiments from about 40 cm to about 120 cm. The length of tubular shaft 704 can be from about 30 cm to about 150 cm, in further embodiments from about 35 cm to about 130 cm and in additional embodiments from about 40 cm to about 120 cm. A person of ordinary skill in the art will recognize that additional ranges of dimensions within the explicit ranges above are contemplated and are within the present disclosure.

Guidewires for neurovascular applications are commercially available. These include TRANSEND® (Stryker) with a distal outer diameter (OD) of 0.014 inches (0.36 mm) and 0.0155 in (0.40 mm) proximal, SYNCHRO® (Stryker) with a range of diameters, CHIKAI™ (Asahi Intecc) with a 0.36 mm diameter and HEADLINER® (MicroVention/Turumo) with a range of diameters available. A guidewire for cerebral vessels with a hyperbolic corewire grind is described in published U.S. patent application 2016/0199620 to Pokorney et al, entitled "Medical Guidewires for Tortuous Vessels," incorporated herein by reference. These guidewires are suitable for the procedures described herein.

Microcatheters are described generally in the previous section, and these can be used in some embodiments without any additional structures mounted on the exterior of the microcatheter. Microcatheters can be formed, for example, with a polymer tube generally with at least a portion of which having metal reinforcement. Various commercially available microcatheters are available for use in the neurovasculature including, for example, Marathon™ (Covidien/Medtronic, 1.3 Fr distal OD), Echelan™ (Covidien/Medtronic, 1.7 Fr distal OD), Nautica™ (Covidien/Medtronic, 2.2 Fr distal OD), Sofia® (Microvention/Turumo), and Excelsior® (Stryker, 1.7 Fr distal OD). These microcatheters or similar devices can be used for the procedures herein, and for appropriate embodiments, these structures can be adapted for use for stent and/or stent retriever delivery.

Referring to FIG. 40, a human patient 560 is shown with a treatment system 562 inserted into their femoral artery 564 where it is guided up the descending aorta 566 to the ascending aorta 568 where it is guided into a carotid artery 570 (left or right) prior to reaching the heart. The distal end of the system is then guided through the patient's neck into an internal carotid artery and then into the cerebral arteries forming the neurovasculature. While this can be a desirable approach to the cerebral arteries, alternative access locations include the arm 572 or the neck 574. While human patients are of particular interest, the devices can be used for farm animals or pet animals.

In the basic procedures described herein, generally a suction catheter and a fiber based filter element are used. This basic procedure is described first, and then some additions to the procedure are subsequently described. Basic procedures using a stent and stent retriever outside of this context are described above in the section where these devices are described. In the basic procedure involving a suction catheter and a fiber based filter, the basic steps are:
1. Place guide catheter in place.
2. Extend guidewire to treatment site with tip past the occlusion.
3. Place suction catheter in position.
4. Guide microcatheter into position with distal tip past occlusion.
5. Remove guidewire.
6. Insert fiber based filter on a guide structure through microcatheter.
7. Push fiber based filter out of the microcatheter to deploy the filter past occlusion.
8. Apply suction and pull fiber based filter toward the suction catheter.
9. Remove clot and devices from patient.

While this order of steps accounts for practical implementation and provides an overview of the procedure, the precise order is not sacrosanct, as will be recognized by a person of ordinary skill in the art. Thus, appropriate steps may be performed in a different order, and some steps can be performed in substeps that may be interspersed with portions of other steps. For example, positioning of the suction catheter may be partially performed prior to placement of the guidewire, while the further positioning of the aspiration catheter may be performed later in the process. Also, repositioning of various components can take place through the procedure as appropriate and desired by the user.

Figure 42:
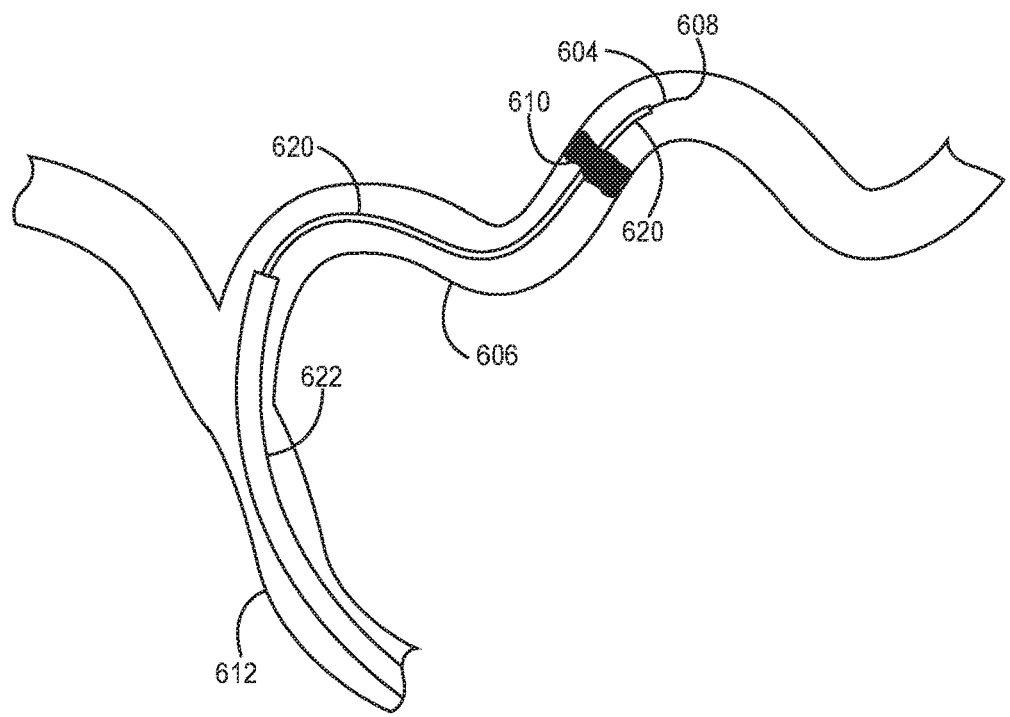
FIG. 42 is a fragmentary view of the cerebral artery of FIG. 41 with a microcatheter extending with its distal end past the clot and an aspiration catheter tip positioned in a proximal location.
Figure 41:
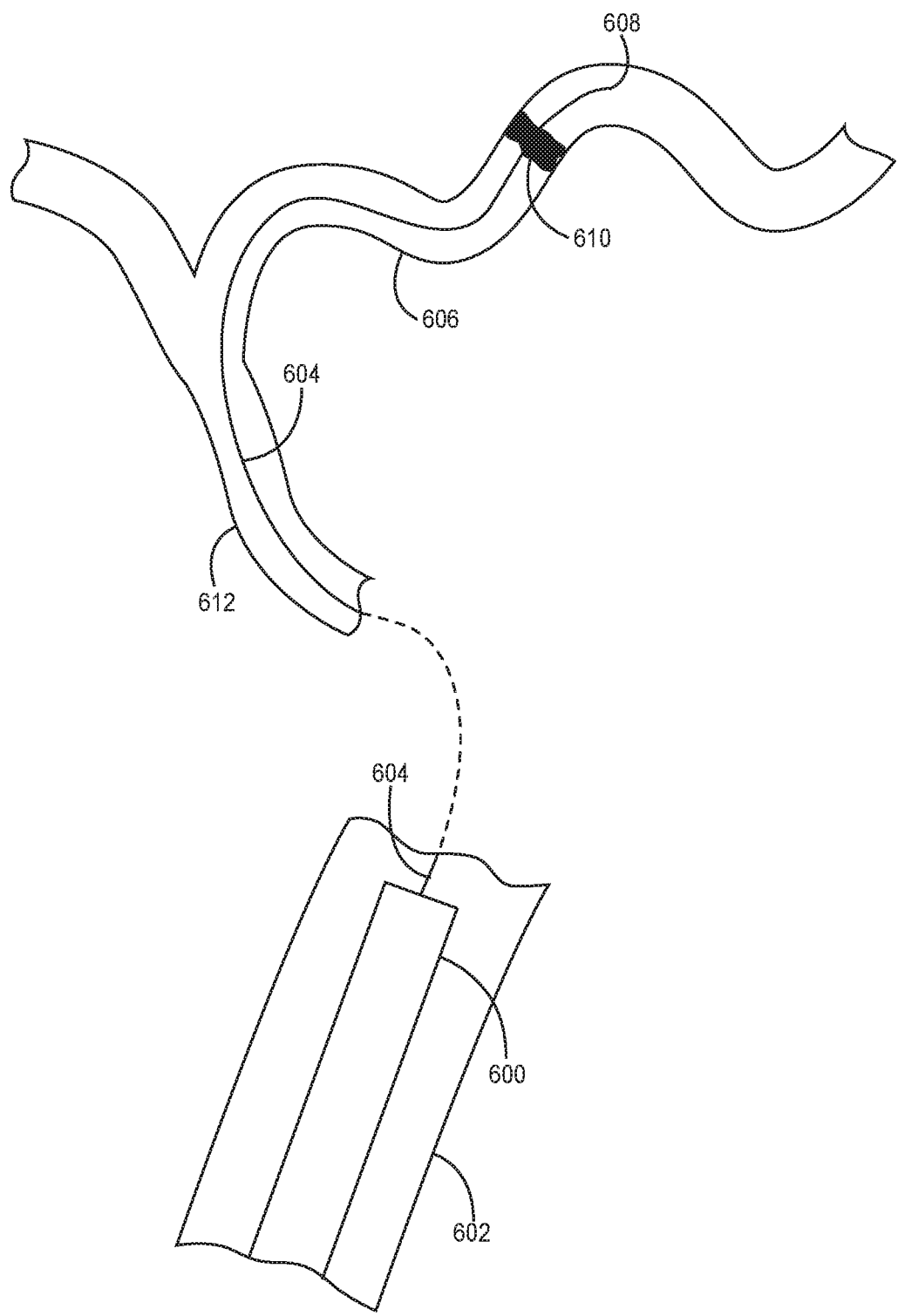
FIG. 41 is a fragmentary view of a section of vasculature with a guide catheter having its distal tip in a carotid artery and a guidewire extending through a clot in a cerebral artery.

Referring to FIG. 41, a guide catheter 600 is placed in the carotid artery 602. A guidewire 604 is guided past carotid artery 602 into a cerebral artery 606 with its distal tip 608 positioned past a clot 610. A vascular path truncated in the figure from carotid artery 602 to an upstream cerebral artery 612 branching into cerebral artery 606 is depicted with a dashed line to note portions of the path not depicted for simplicity of drawing. Referring to FIG. 42, a microcatheter 620 is positioned over guidewire 604 with its distal tip past clot 610. Aspiration catheter distal tip 622 is positioned entering cerebral artery 606. Depending on the specifics of the vasculature and the aspiration catheter design, aspiration catheter distal tip may be brought closer or further from clot 610. The medical professional can adjust the procedure accordingly based on the position of the aspiration catheter.

Figure 43:
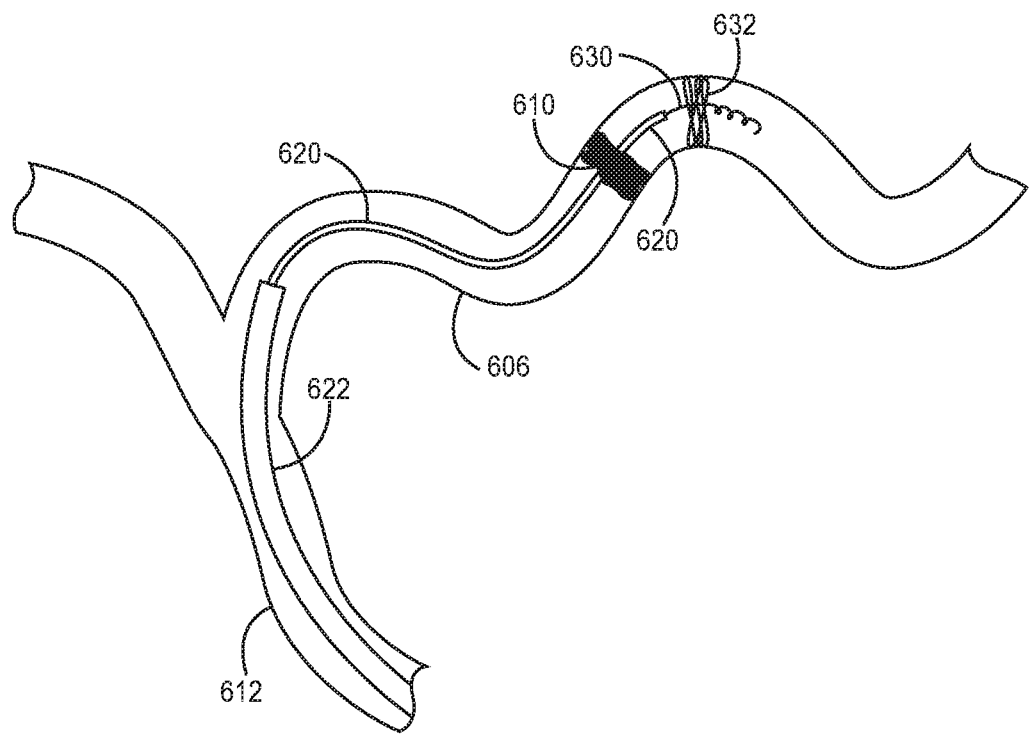
FIG. 43 is a fragmentary view of the cerebral artery of FIG. 42 with the guidewire removed and replaced with a guide structure supporting a deployed fiber based filter.
Figure 44:
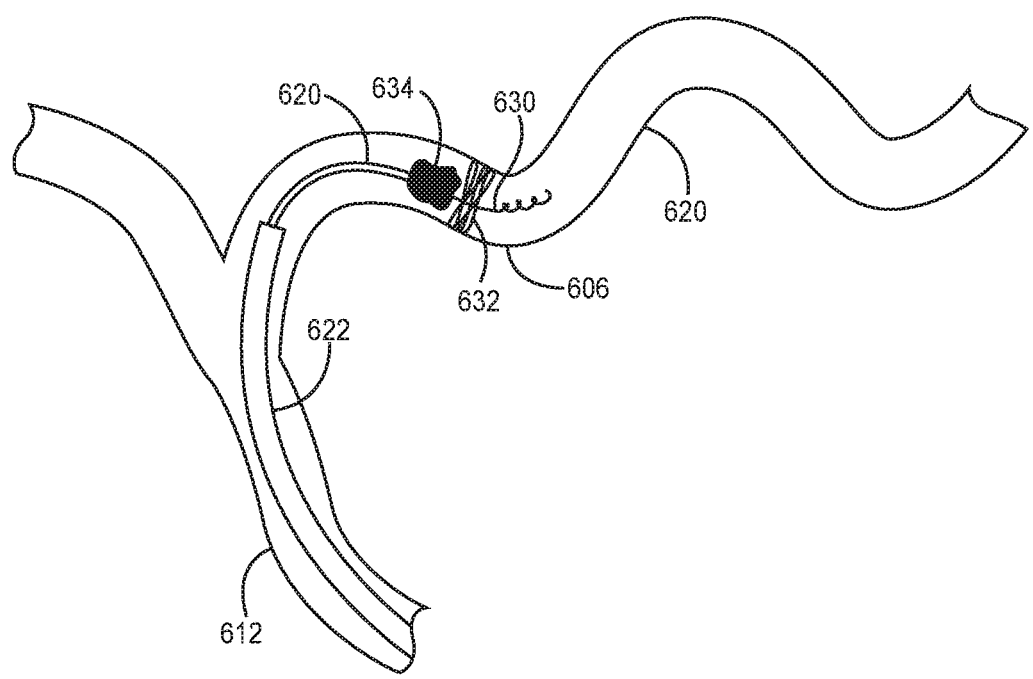
FIG. 44 is a fragmentary view of the cerebral artery of FIG. 43 in which the clot or portion thereof has been pulled part of the way with the aspiration catheter using the filter to engage the clot.
Figure 45:
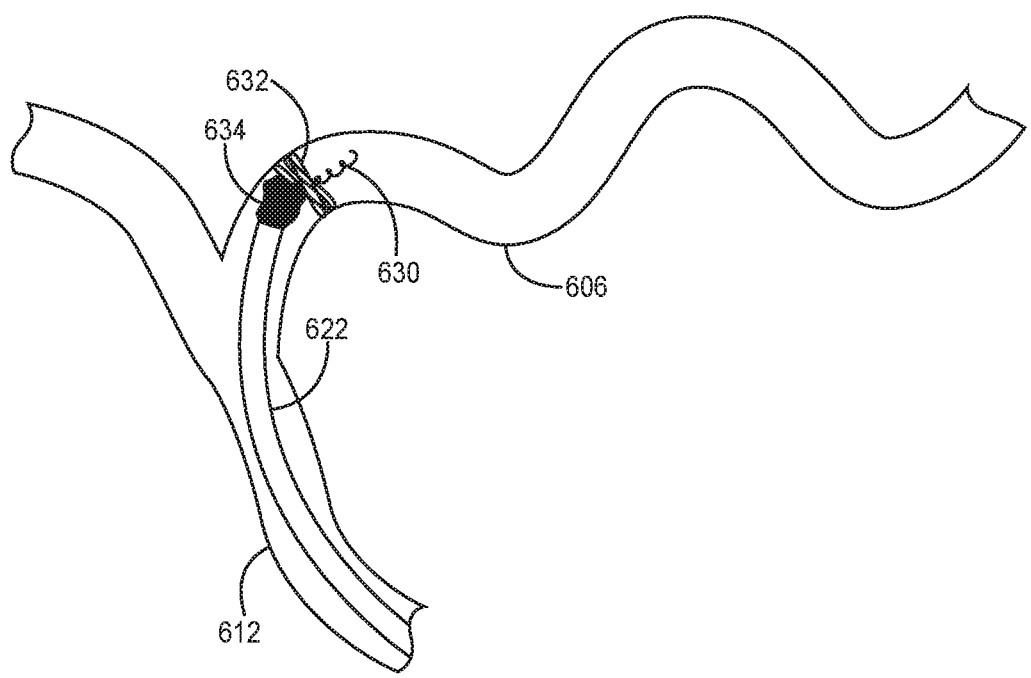
FIG. 45 is a fragmentary view of the cerebral artery of FIG. 44 in which the clot or portion thereof have been pulled to the opening of the aspiration catheter.
Figure 46:
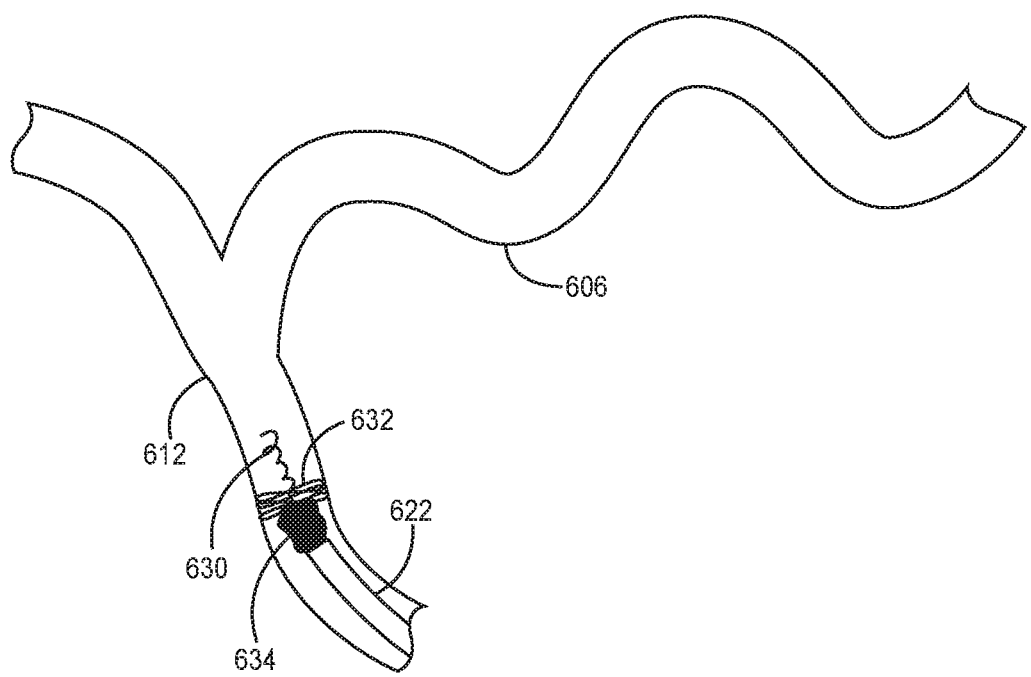
FIG. 46 is a fragmentary view of the cerebral artery of FIG. 45 in which the aspiration catheter, clot or fragment thereof and the filter are being removed from the patient.

With the microcatheter in position, guidewire 604 can be removed and a guide structure 630 with a fiber based filter 632 can be put in position with the filter deployed distal to clot 610. Referring to FIG. 43, fiber based filter 632 is shown in a deployed position past clot 610. In embodiments in which other treatment components are not used for clot removal, aspiration can be initiated through aspiration catheter distal tip 622, and the fiber based filter can be pulled in a proximal direction toward the aspiration catheter distal tip 622, as shown in FIG. 44. Engaged clot 634 may be pulled by fiber based filter 632 or clot 634 can be more directly transitioned to the aspiration catheter by the suction. Engaged clot 634 may or may not include all of clot 610 depending on if any fragments are shed by clot 610 during movement. Any fragments may be removed by the aspiration, or they may be trapped by fiber based filter 632 for subsequent removal. While FIG. 43 shows fiber based filter being deployed distal to the clot, the fiber based filter can be deployed at the clot so that the fiber directly engages the center of the clot. Preliminary clinical tests have achieved desired clot removal with this approach in combination with aspiration, so that this delivery approach may be a suitable option for the procedure.

As shown in FIGS. 43-46, an aspiration catheter or tip thereof can be held fixed while the clot or portion thereof is brought to the tip of the aspiration catheter. However, in additional or alternative embodiments, the aspiration catheter can be moved during this portion of the procedure if desired. The amount of fluid aspirated can be selected by the medical professional to achieve desired performance. A moderate amount of blood may be removed, and with the suction available through commercial aspiration catheters, some trauma to the blood vessel may result from the pressure changes associated with the aspiration and the termination of the aspiration. To ameliorate these pressure changes at least to some degree, fluid can be profused through the microcatheter. The fluid can be buffered saline, blood (either from the patient or a compatible donor) or other suitable biocompatible fluid. Due to the smaller diameter of the microcatheter, the profused fluid may not compensate for the aspirated fluid, but reduction of pressure changes can be desirable. Also, the profused fluid can further flush any clot fragments toward the aspiration catheter to lower risk of distal embolization.

Embodiments of treatment components with a stent and stent retriever have been described above. These components can be used in distinct procedures as noted in the above section, but these components can also be incorporated in the procedure of FIGS. 41-46. For example, starting with the configuration in FIG. 43, the additional treatment components can be delivered to the clot. A specific procedure is described with a stent retriever mounted on the surface of the micro catheter and a stent delivered from the interior of the microcatheter. Based on the description above, a person of ordinary skill in the art will appreciate the steps for the alternative use of devices with a stent provided on the surface of the microcatheter and the stent retriever delivered from the interior of the microcatheter.

Figure 48:
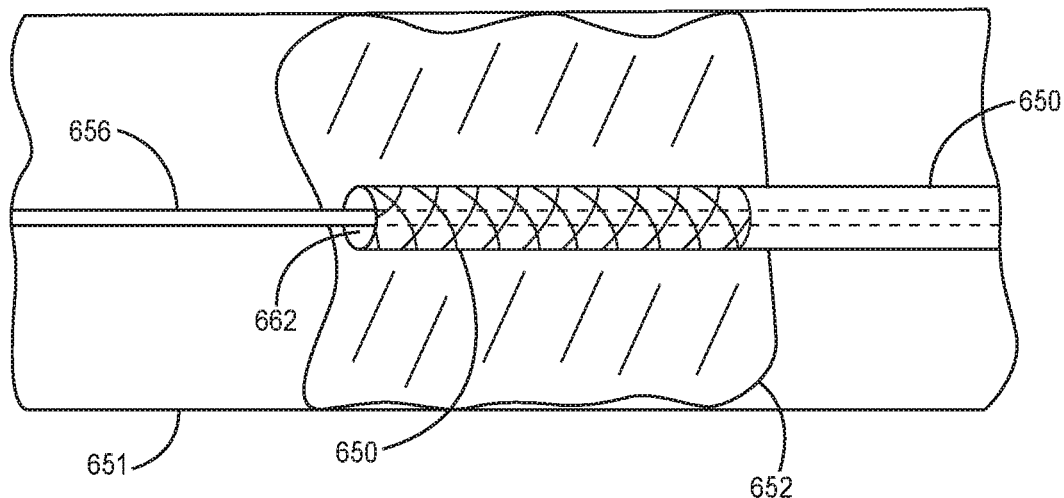
FIG. 48 is a fragmentary side view of the microcatheter tip and treatment structures of FIG. 47 positioned within the clot.
Figure 49:
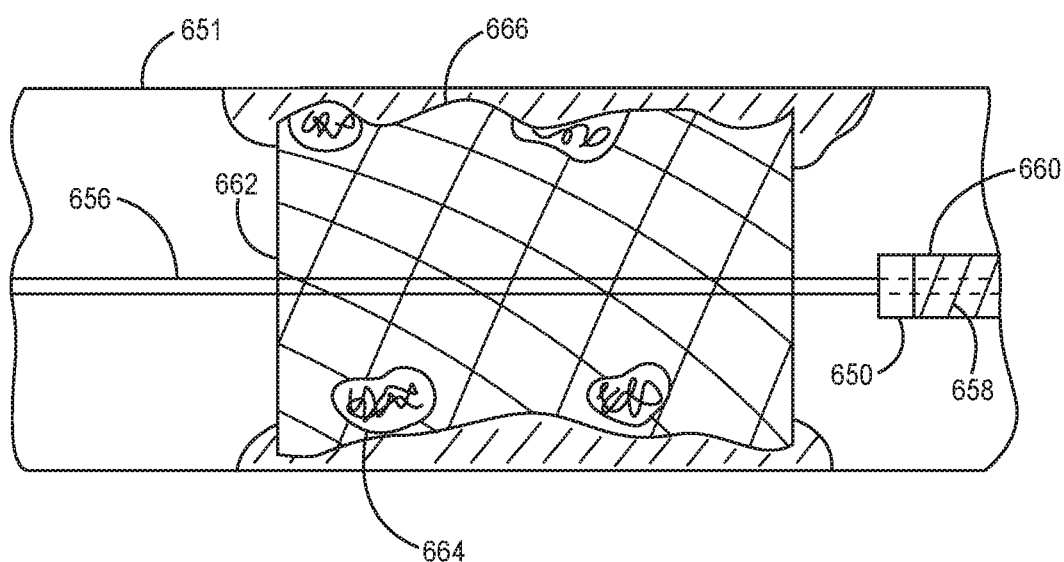
FIG. 49 is a fragmentary side view of the vessel with a stent deployed at the clot and the microcatheter positioned just proximal to the deployed stent.

With the fiber based filter deployed, the stent can be delivered to the location of the clot(s). In embodiments of particular interest, the stent can be delivered in association with the microcatheter over the guide structure supporting a fiber based filter element. Referring to FIG. 47, microcatheter 650 is delivered into artery 651 with its distal end past clot 652 to facilitate placement of fiber based filter 654 supported on guide structure 656 in a deployed configuration past clot 652. In this embodiment, microcatheter 650 can have a first treatment device 658 on its surface under a sheath 660 and a second treatment device 662 within its lumen. In the following figures, first treatment device is depicted as a stent retriever and second treatment device is depicted as a stent, but in alternative embodiments, first treatment device is a stent and second treatment device is a stent retriever or other atherectomy device. Prior to deployment, second treatment device (stent) 662 can be positioned at the location of clot 652, as shown in FIG. 48 The stent can be deployed through the movement of microcatheter 650 in a proximal direction while maintaining the position of second treatment device (stent) 662, for example, using a push rod or the like within the microcatheter. With a self extending stent, the stent then deploys within the clot, as shown in FIG. 49.

A self-extending stent may offer a desirable feature of encouraging further extension of the stent during the procedure as portions of the clot are removed. Correspondingly, the aspiration catheter can apply suction during the stent deployment to reduce any embolic load received by the filter and reduce the risk of distal embolization. Since the stent is deployed at the location of the clot, portions 664 of the clot can infiltrate portions of the second treatment device (stent) into the stent lumen following deployment of the stent, as shown in FIG. 49 with remaining portions of the clot 666 located between deployed second treatment device (stent) 662 and vessel 651.

First treatment device (stent retriever) 658 can then be deliver from the surface of microcatheter 650 to place a scrapping structure in the lumen of the stent, as shown in FIG. 50. Prior to release of the first treatment device (stent retriever), microcatheter 650 can be advanced in a distal direction after release of second treatment device (stent) 662 to position first treatment device (stent retriever) 658 within the stent lumen. With first treatment device (stent retriever) 658 in a desired position, sheath 660 can be withdrawn in a proximal direction relative to microcatheter 650 to release first treatment device (stent retriever) 658, which can deploy if self extending. First treatment device (stent retriever) 658 can be pulled in a proximal direction to dislodge additional portions of the clot with protection to the vessel wall provided by second treatment device (stent) 662. If appropriate, the abrading process can be repeated one, two, three or more times with the scraping structure moved in a distal direction relative to engage the clot within the stent again. Second treatment device (stent) 662 generally provides a limit to the extension of first treatment device (stent retriever) 658. As fragments of the clot are dislodged, the frame of first treatment structure (stent retriever) 658 and second treatment structure (stent) 662 may be able to extend further radially in the vessel. Further extension of the structures may allow for the dislodging of additional clot fragments. Dislodging of clot fragments can provide a more open lumen of the artery. Suction may be applied during the fragmentation process with aspiration catheter 668. A depiction of the overall system with appropriate protections of the filter and the aspiration catheter are depicted in FIG. 50.

Use of the atherectomy element can be completed based on either observations of the vessel flow suggesting the clot removal process appears to have dislodged a desired amount of the clot and/or based on an estimated period of time to complete the desired clot removal process and/or some other suitable approach to control the clot removal process. Once the clot removal process is completed, the atherectomy element can be removed from the vessel, which may or may not involve removal of an aspiration catheter. In some embodiments, the atherectomy element and/or the filter (embolic protection) element can be pulled into an aspiration catheter or the like positioned proximal to the treatment site for removal from the patient. The stent should safely remain at the delivered location.

The fiber based, filter can be removed simultaneous with the atherectomy element or subsequent to the removal of the atherectomy element. In some embodiments, aspiration can be applied during the removal of the filter. The filter can be maintained in its extended configuration during at least a portion of the movement of the filter in a distal to proximal direction to sweep the corresponding portion of the vessel. The movement of the filter element generally can be continued through the stent to remove any loosened portion of the clot that had not been previously removed. The filter can be translated to the opening of the aspiration catheter with or without allowing the fibers to assume a lower profile configuration. In some embodiments, the filter element can be removed from the patient with the aspiration catheter.

The procedure can be designed for relatively safe operation with distal protection provided by the filter to catch any emboli generated, the aspiration catheter to remove debris from the vessel at more or more points of time in the procedure and the stent positioned to allow application of the atherectomy cutting element with reduced or eliminated risk of damage to the vessel wall. While the procedure is designed for safety, it is expected that the procedure can be effective with a relatively aggressive approach at clot removal with the mechanical cutting element.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A filter device having an un-deployed low profile configuration and an unconstrained deployed configuration comprising a guide structure, an anchor secured at a fixed location on the guide structure having a central axis, a slide positioned over the guide structure, a filter cartridge secured on one end to the anchor and on the other end to the slide, wherein the filter cartridge comprises a plurality of unwoven polymer fibers in a bundle in the un-deployed low profile configuration, and one or more metal elements radially below relative to the central axis of the bundle of polymer fibers secured around the guide structure, wherein moving the slide closer to the anchor transitions the metal elements to the unconstrained deployed configuration with the metal elements forming a curved structure extending radially outward, wherein the device in the unconstrained deployed configuration further comprises the furthest radial extent of the metal elements being below a mat of fibers, and wherein the metal elements have an unconstrained radial extent no more than about 94% of the furthest unconstrained radial extent of the polymer fibers.

2. The filter device of claim 1 wherein the metal elements comprise three or more unbraided elements.

3. The filter device of claim 1 wherein metal elements comprise braided wires.

4. The filter device of claim 1 wherein the metal elements comprise three to ten elements with a circumference from about 0.0005 inches (12 microns) to about 0.025 inches (600 microns).

5. The filter device of claim 1 wherein the filter cartridge further comprises metal wires in the bundle with the polymer fibers from about 1% to about 10% of the number of strands being metal wire and having a diameter from about 0.0001 inches (2.4 microns) to about 0.002 inches (48 microns).

6. The filter device of claim 1 wherein the filter cartridge is self actuating, wherein the metal elements comprise a spring metal with a shape memory that assumes a pre-selected shape upon release of constraint of the filter cartridge.

7. The filter device of claim 1 further comprising an overtube connected to the slide and extending in a proximal direction over the guide structure, wherein relative movement of the overtube and the guide structure transitions the filter cartridge from the un-deployed low profile configuration to the unconstrained deployed configuration, wherein the filter cartridge extends radially.

8. The filter device of claim 7 wherein the overtube comprises a polymer tube.

9. The filter device of claim 1 wherein the metal elements have an unconstrained radial extent no more than about 90% of the furthest unconstrained radial extent of the polymer fibers.

10. The filter device of claim 1 wherein the polymer fibers comprise polyamides (e.g., nylon), polyesters (e.g., polyethylene terephthalate), polyacetals/polyketals, polyimide, polystyrenes, polyacrylates, vinyl polymers (e.g., polyethylene, polytetrafluoroethylene, polypropylene and polyvinyl chloride), polycarbonates, poly dimethyl siloxanes, cellulose acetates, polymethyl methacrylates, polyether ether ketones (PEEK), ethylene vinyl acetates, polysulfones, nitrocelluloses, similar copolymers and mixtures thereof.

11. The filter device of claim 1 wherein the metal wires are radiopaque.

12. The filter device of claim 1 wherein the metal wires extend into a curved structure.

13. The filter device of claim 12 wherein the extended curved metal wires form petal shaped features around an open interior.

* * * * *